United States Patent
Birdsall et al.

(10) Patent No.: US 11,761,932 B2
(45) Date of Patent: Sep. 19, 2023

(54) RPLC-BASED PEPTIDE MAPPING CHROMATOGRAPHIC PERFORMANCE USING METAL CHELATORS AS MOBILE PHASE ADDITIVES

(71) Applicant: Waters Technologies Corporation, Milford, MA (US)

(72) Inventors: Robert Birdsall, Westborough, MA (US); Ying Qing Yu, Uxbridge, MA (US); Jacob Kellett, Whitinsville, MA (US)

(73) Assignee: Waters Technologies Corporation, Milford, MA (US)

( * ) Notice: Subject to any disclaimer, the term of this patent is extended or adjusted under 35 U.S.C. 154(b) by 377 days.

(21) Appl. No.: 16/893,537

(22) Filed: Jun. 5, 2020

(65) Prior Publication Data
US 2020/0386722 A1 Dec. 10, 2020

Related U.S. Application Data

(60) Provisional application No. 62/883,182, filed on Aug. 6, 2019, provisional application No. 62/858,380, filed on Jun. 7, 2019.

(51) Int. Cl.
| | | |
|---|---|---|
| *G01N 33/68* | (2006.01) | |
| *G01N 33/15* | (2006.01) | |
| *C12Q 1/37* | (2006.01) | |
| *G01N 1/40* | (2006.01) | |
| *G01N 30/08* | (2006.01) | |
| *G01N 30/72* | (2006.01) | |
| *G01N 30/74* | (2006.01) | |

(52) U.S. Cl.
CPC .............. *G01N 30/08* (2013.01); *C12Q 1/37* (2013.01); *G01N 1/405* (2013.01); *G01N 1/4044* (2013.01); *G01N 30/7233* (2013.01); *G01N 30/74* (2013.01); *G01N 33/15* (2013.01); *G01N 33/6848* (2013.01)

(58) Field of Classification Search
CPC ...... B01D 15/166; B01D 15/325; C12Q 1/37; G01N 1/4044; G01N 1/405; G01N 2030/8813; G01N 30/08; G01N 30/34; G01N 30/7233; G01N 30/74; G01N 33/15; G01N 33/68; G01N 33/6848; G01N 33/92; Y10T 436/24
USPC ...... 435/23; 436/86, 89, 161, 164, 172, 173; 422/70, 82.08
See application file for complete search history.

(56) References Cited

U.S. PATENT DOCUMENTS

| | | | | |
|---|---|---|---|---|
| 4,909,941 | A | * 3/1990 | Poll .......................... | C07K 1/16 530/371 |
| 2011/0033378 | A1* | 2/2011 | Dimasi ................... | A61P 35/02 424/1.49 |
| 2017/0184555 | A1* | 6/2017 | Birdsall ............... | C12Q 1/6816 |
| 2019/0064126 | A1 | 2/2019 | Hsiao et al. | |

FOREIGN PATENT DOCUMENTS

EP 3187879 A1 7/2017

OTHER PUBLICATIONS

Birdsall et al. "Application of mobile phase additives to reduce metal-ion mediated adsorption of non-phosphorylated peptides in RPLC/MS-based assays." J. Chromatogr. B. 1126-1127(2019): 121773.
Hsiao et al. "Improved LC/MS Methods for the Analysis of Metal-Sensitive Analytes Using Medronic Acid as a Mobile Phase Additive." Anal. Chem. 90.15(2018): 9457-9464.
Invitation to Pay Additional Fees and, Where Applicable, Protest Fee issued in International Application No. PCT/IB2020/055334 dated Sep. 22, 2020.

* cited by examiner

*Primary Examiner* — Maureen Wallenhorst
(74) *Attorney, Agent, or Firm* — WOMBLE BOND DICKINSON (US) LLP; Deborah M. Vernon; Dennis J. Parad

(57) ABSTRACT

The present technology relates to a method of analyzing a sample including an analyte. The method includes injecting the sample including the analyte into a mobile phase. The mobile phase includes a metal chelator additive having a concentration between about 1 ppm to about 10 ppm. The method also includes separating the analyte using liquid chromatography and analyzing the analyte using a mass spectrometer, an ultra-violet detector, or a combination thereof.

15 Claims, 34 Drawing Sheets

Specification includes a Sequence Listing.

MP A: H₂O, 0.1%FA (MS grade)
MP B: MeCN, 0.1% FA (MS grade)

| Time (min) | Flow (mL/min) | %A | %B |
|---|---|---|---|
| 0.00 | 0.200 | 99.0 | 1.0 |
| 2.00 | 0.200 | 99.0 | 1.0 |
| 52.00 | 0.200 | 65.0 | 35.0 |
| 58.00 | 0.200 | 15.0 | 85.0 |
| 62.00 | 0.200 | 15.0 | 85.0 |
| 67.00 | 0.200 | 99.0 | 1.0 |
| 80.00 | 0.200 | 99.0 | 1.0 |

Column: CSH 2.1x100mm, 1.7 um C18
Temp: 60C
FC: 10mm analytical, 214nm, 10Hz

QDa:
Probe = 600C
Cone = 10V
Capillary = 1.5 kV

FIG. 2D

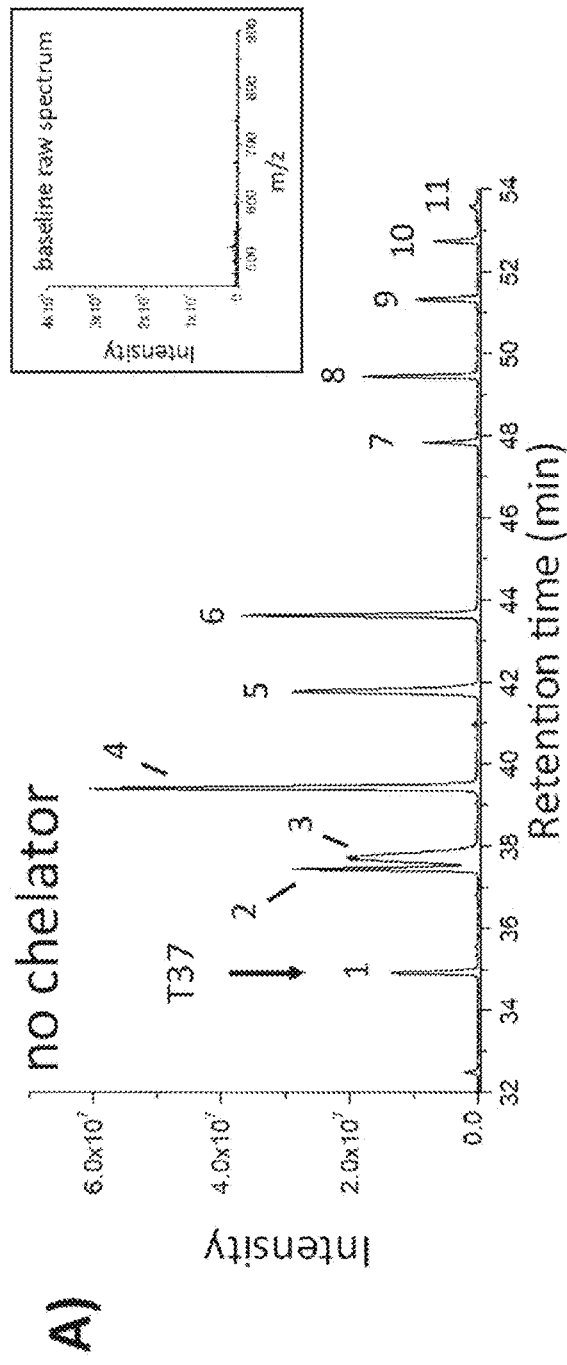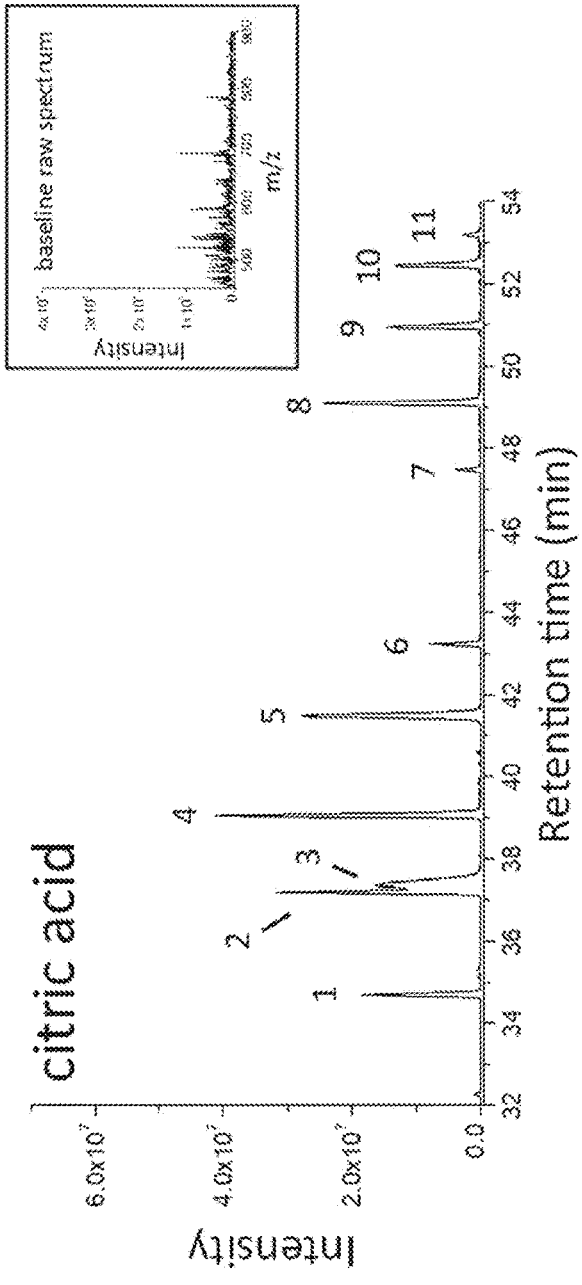

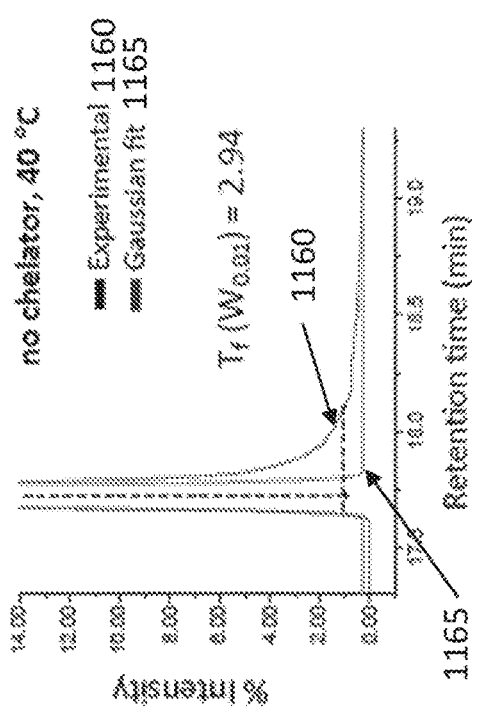
FIG. 11F
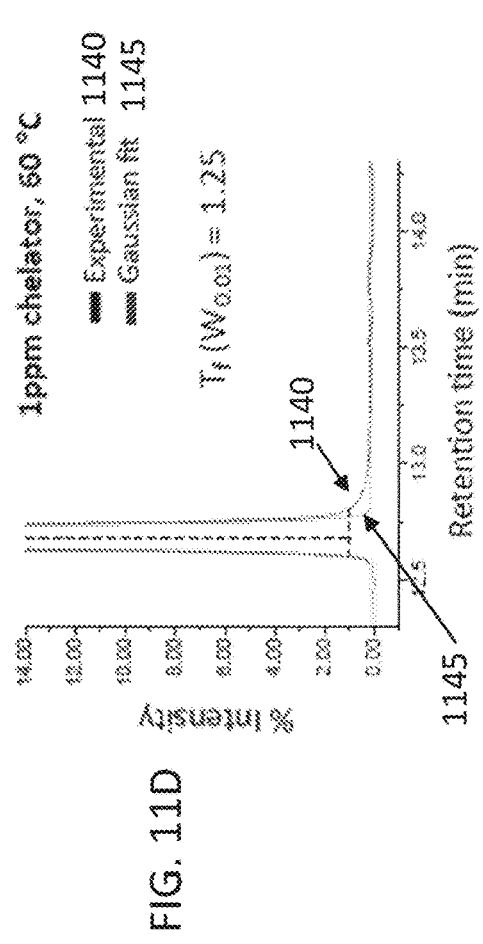
FIG. 11D
FIG. 11E
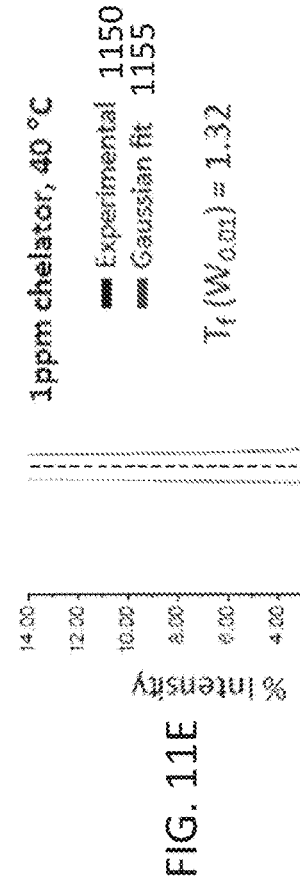

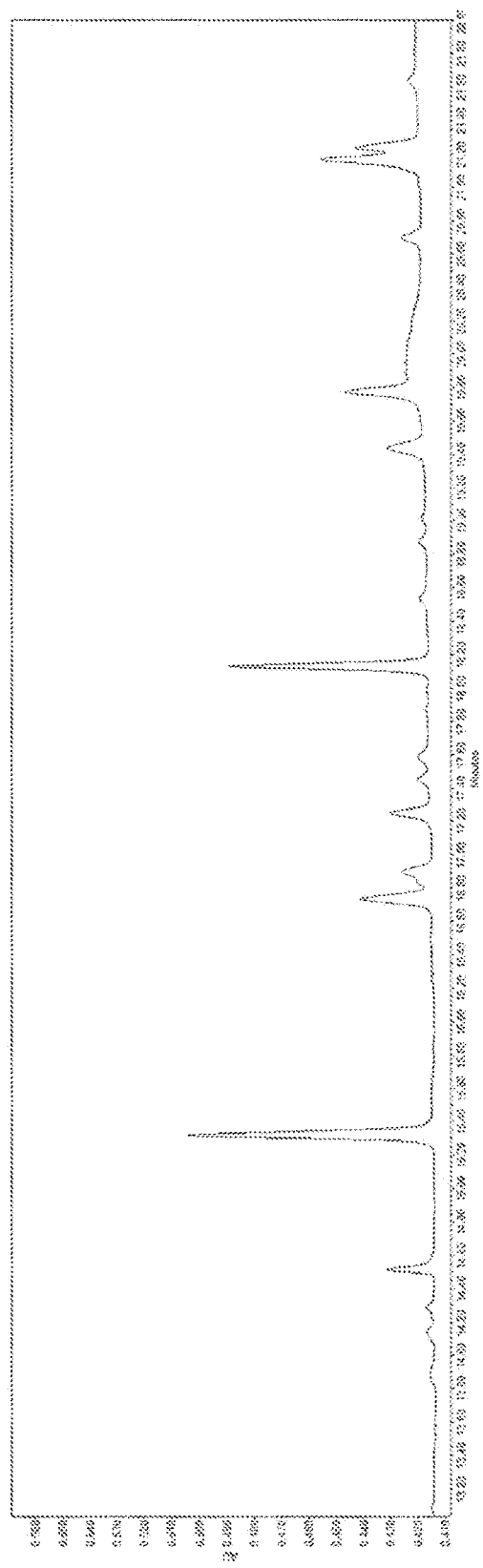
FIG. 13A: chelator not present
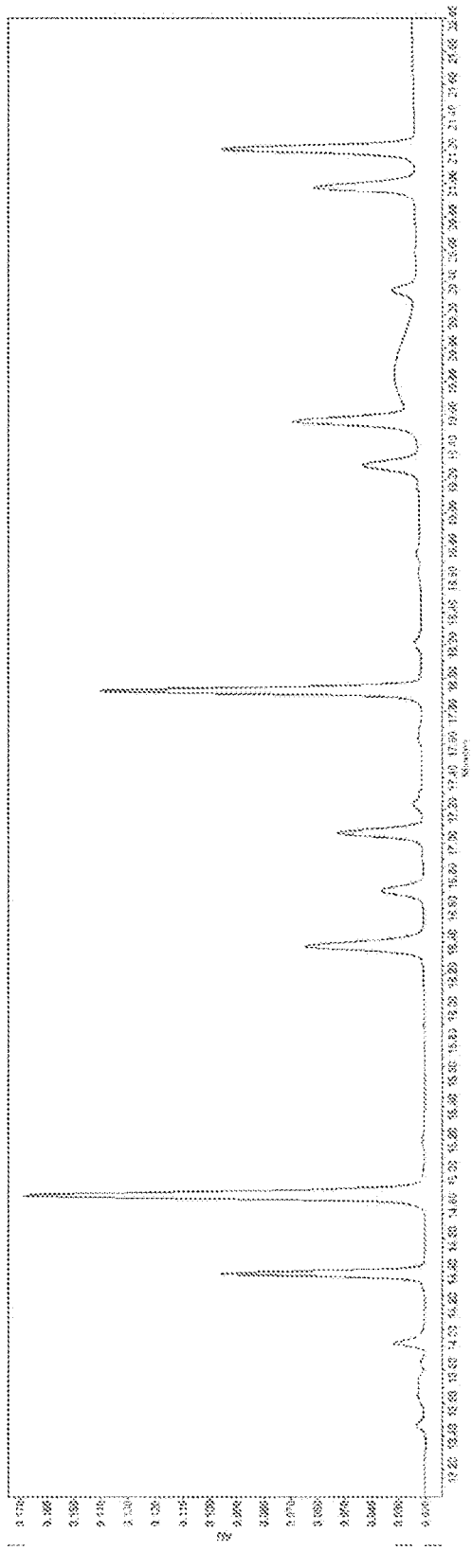
FIG. 13B chelator present

AS-FTN
- Sample temp 10 °C

Binary Pump
- Mixer volume = 250 uL
MP A = 90% Water, 10% Acetonitrile, 0.1% Formic Acid, Additive*
MP B = 90% Acetonitrile, 10% Water, 0.1% Formic Acid, Additive*

CM-A (column heater)
- Column temp 60 °C
- Column CSH 2.1 x 100 mm, 1.7 um

TUV
- 10mm analytical flow cell
- Sampling rate 10 Hz, λ = 214nm

QDa
- TIC (450 – 1250 m/z)
- SIR: 849.20 m/z
- SIR: 849.60 m/z
- 2 Hz sampling rate

*Additives = 1ppm: citric acid OR sodium citrate OR isocitrate OR ammonium citrate dibasic OR ammonium citrate tribasic OR medronic acid OR ammonium formate OR 5uM Agilent InfinityLab Additive Gradient:

| Time (min) | Flow (mL/min) | %A | %B | Curve |
|---|---|---|---|---|
| Initial | 0.250 | 99.0 | 1.0 | Initial |
| 5.00 | 0.250 | 99.0 | 1.0 | 6 |
| 65.00 | 0.250 | 65.0 | 35.0 | 6 |
| 68.00 | 0.250 | 30.0 | 70.0 | 6 |
| 70.00 | 0.250 | 30.0 | 70.0 | 6 |
| 71.00 | 0.250 | 99.0 | 1.0 | 6 |
| 87.00 | 0.250 | 99.0 | 1.0 | 6 |

FIG. 15

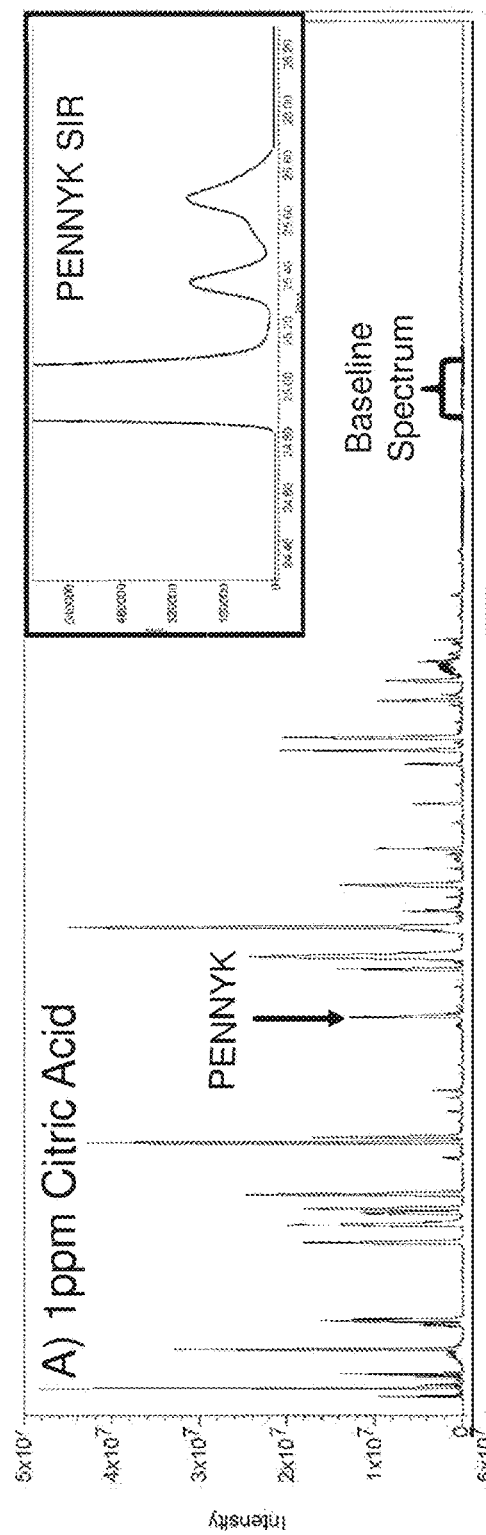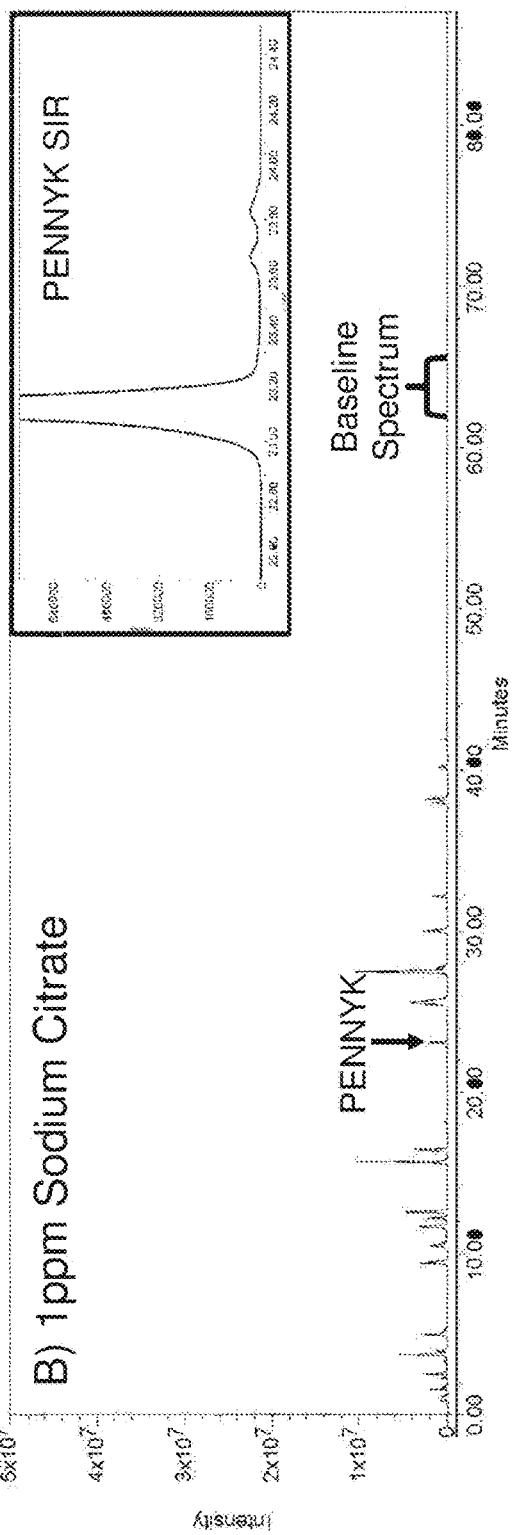
FIG. 16A
FIG. 16B

C) 1ppm Citric Acid

D) 1ppm Sodium Citrate

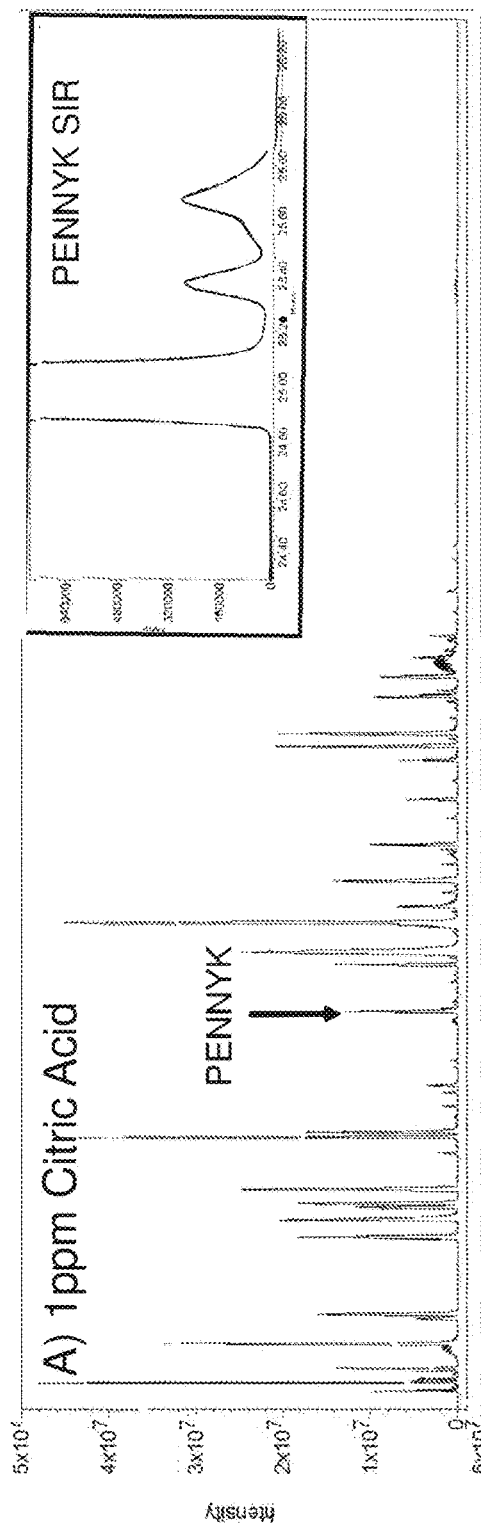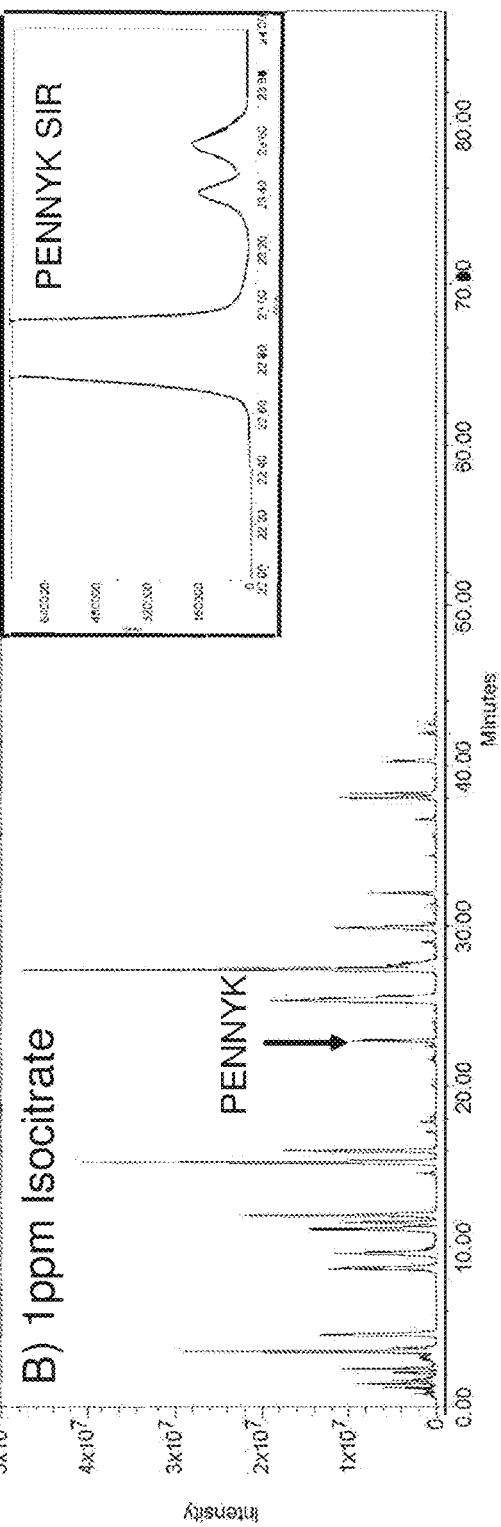
FIG. 17A
FIG. 17B

C) 1ppm Citric Acid

D) 1ppm Isocitrate

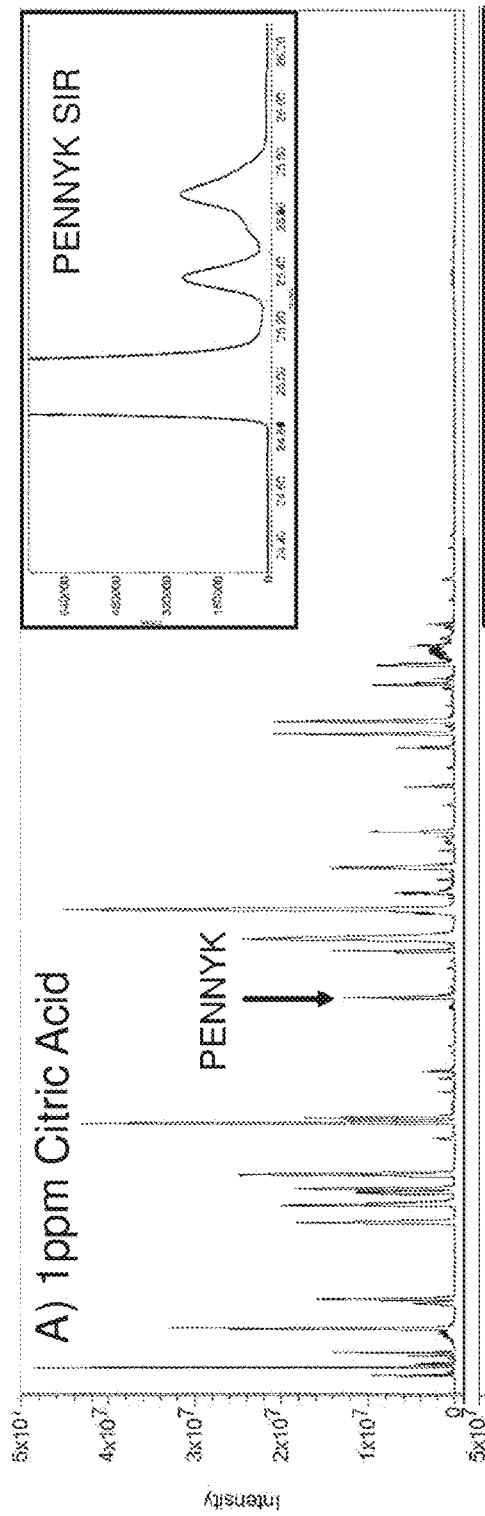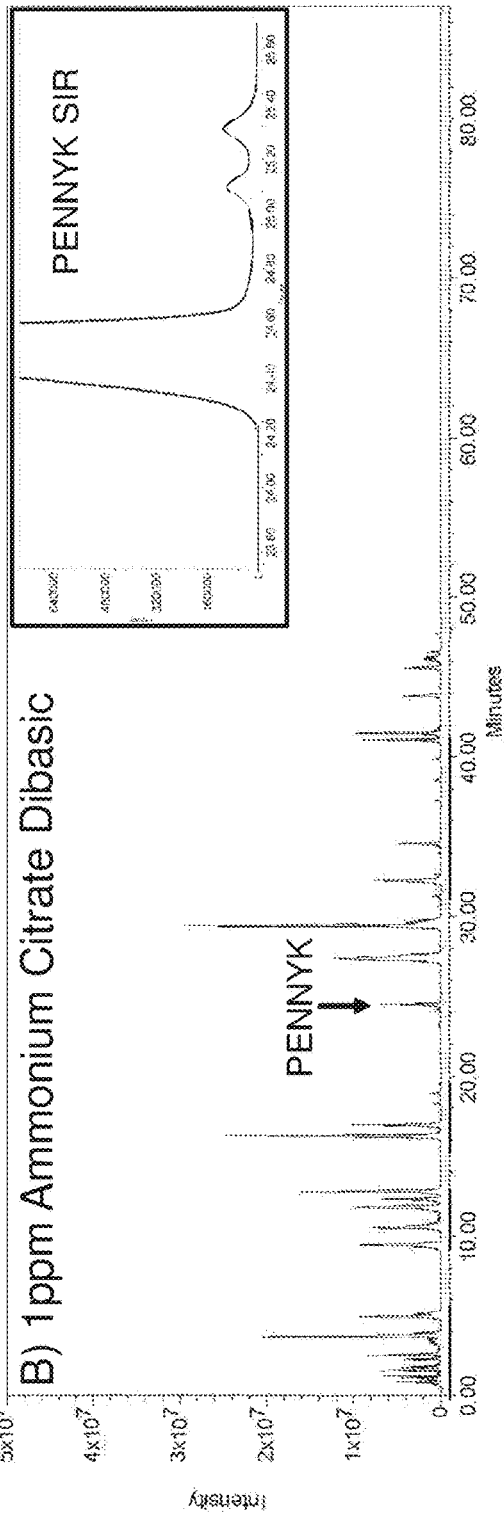
FIG. 18A
FIG. 18B

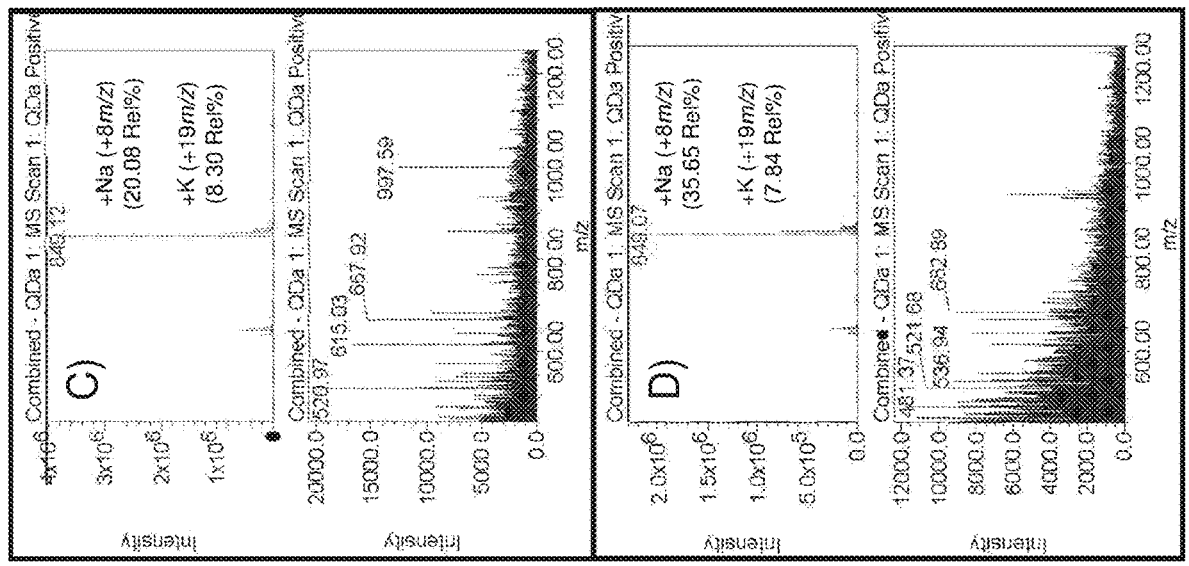

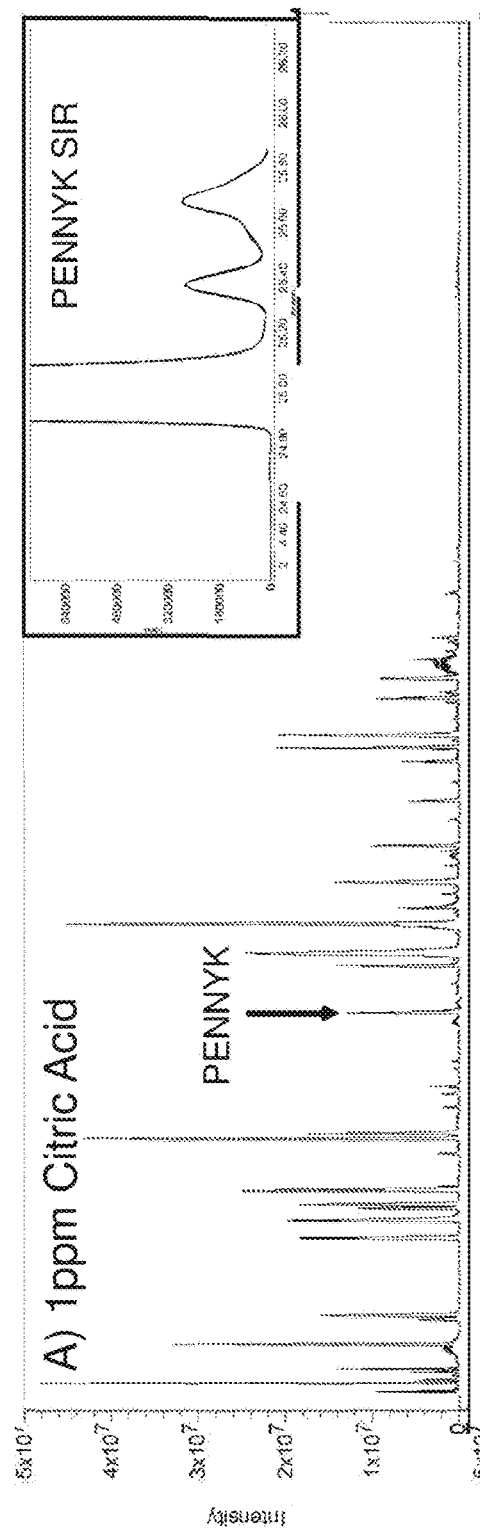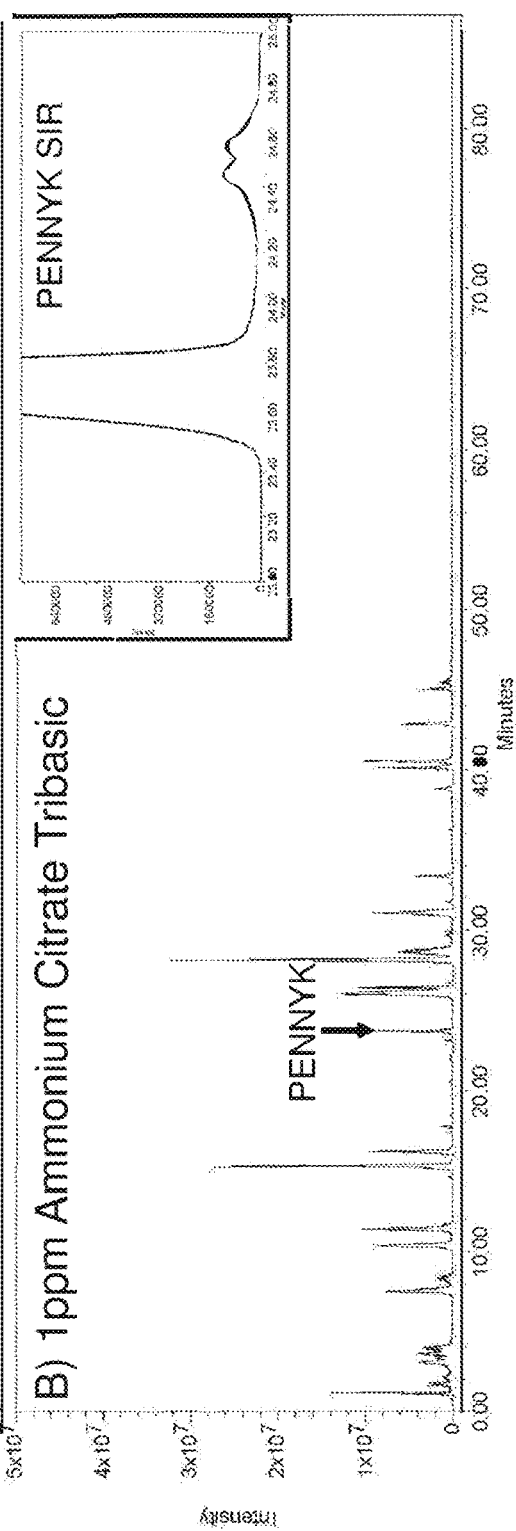
FIG. 19A
FIG. 19B

C) 1 ppm Citric Acid

D) 1 ppm Ammonium Citrate Tribasic

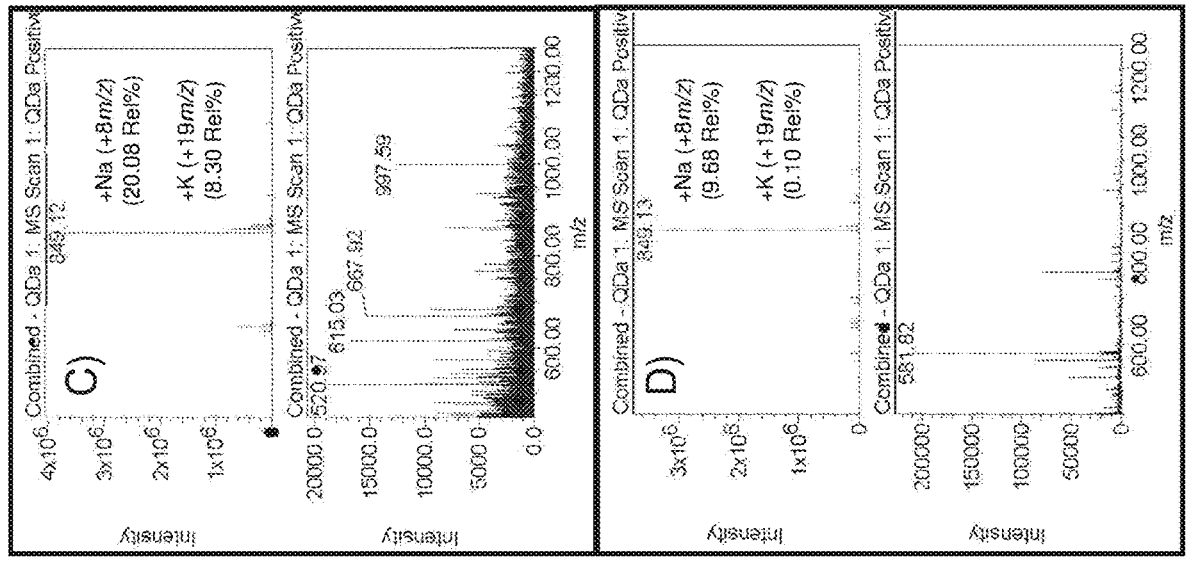
FIG. 20C  C) 1ppm Citric Acid
FIG. 20D  D) 1ppm Medronic Acid

FIG. 21 *Prepared at 5uM per Agilent manufacturer instructions
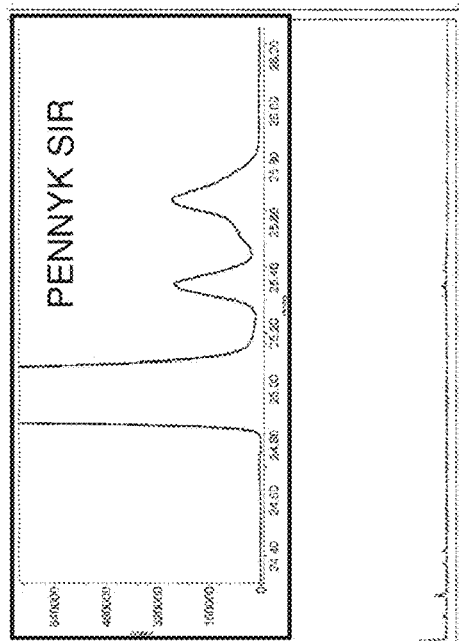
FIG. 21A
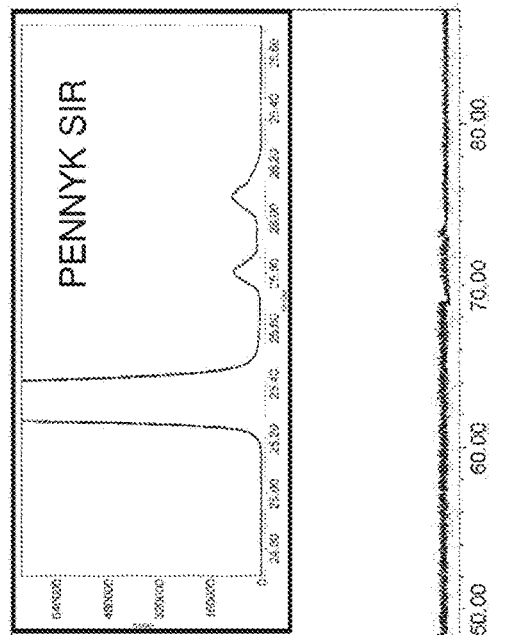
FIG. 21B
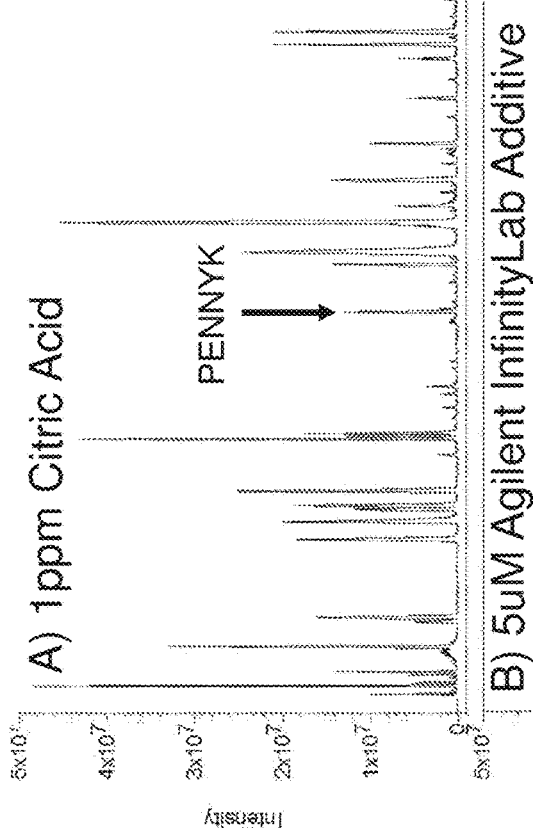
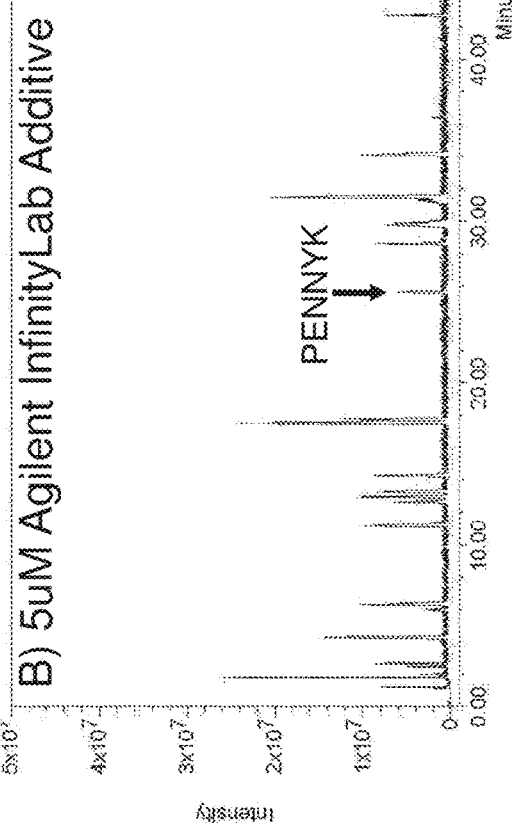

C) 1ppm Citric Acid

D) 5uM Agilent InfinityLab Additive

SEQUENCE LISTING

```
<160> NUMBER OF SEQ ID NOS: 4

<210> SEQ ID NO 1
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 1

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 2
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 2

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25

<210> SEQ ID NO 3
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 3

Val Asp Asn Ala Leu Gln Ser Gly Asn Ser Gln Glu Ser Val Thr Glu
1               5                   10                  15

Gln Asp Ser Lys
            20

<210> SEQ ID NO 4
<211> LENGTH: 6
<212> TYPE: PRT
<213> ORGANISM: Artificial Sequence
<220> FEATURE:
<223> OTHER INFORMATION: Synethic polypeptide

<400> SEQUENCE: 4

Pro Glu Asn Asn Tyr Lys
1               5
```

RPLC-BASED PEPTIDE MAPPING CHROMATOGRAPHIC PERFORMANCE USING METAL CHELATORS AS MOBILE PHASE ADDITIVES

CROSS-REFERENCE TO RELATED APPLICATIONS

This application claims priority to and benefit of U.S. provisional patent application No. 62/858,380, filed on Jun. 7, 2019 and entitled "RPLC-BASED PEPTIDE MAPPING CHROMATOGRAPHIC PERFORMANCE USING METAL CHELATORS AS MOBILE PHASE ADDITIVES" the entire contents of which are hereby incorporated by reference. This application also claims priority to and benefit of U.S. provisional patent application No. 62/883,182, filed on Aug. 6, 2019 and entitled "RPLC-BASED PEPTIDE MAPPING CHROMATOGRAPHIC PERFORMANCE USING METAL CHELATORS AS MOBILE PHASE ADDITIVES" the entire contents of which are hereby incorporated by reference.

SEQUENCE LISTING

The instant application contains a Sequence Listing which has been filed electronically in ASCII format and is hereby incorporated by reference in its entirety. Said ASCII copy, created on Jun. 18, 2020, is named W4077US03_ST25.txt and is 1.41 KB in size.

FIELD OF THE TECHNOLOGY

The present disclosure relates to improving chromatographic performance for reverse phase liquid chromatography (RPLC) based peptide mapping using metal chelators as mobile phase additives. More specifically, the present disclosure relates to a method of analyzing a sample comprising an intact protein for peptide mapping or a fatty acid that includes using citric acid as a mobile phase additive at a concentration of between about 1 ppm to about 10 ppm.

BACKGROUND

Peptide level analysis of protein modifications is one of the primary analytical methods regularly performed throughout the lifecycle of therapeutic proteins. It has proven to be an invaluable tool in the elucidation of structural information during the discovery and/or characterization phase of protein-based therapeutics as well as assessing product and/or process related impurities in the development of control strategies as part of process development. As a monitoring tool, peptide mapping is regularly deployed in the manufacturing setting as an identity assay as well as a lot release assay to ensure drug product safety. More recently, peptide mapping has seen deployment as a multi-attribute monitoring (MAM) technique to improve productivity and data quality by effectively and directly monitoring multiple potential critical quality attributes (pCQAs) simultaneously.

Peptide mapping workflows rely on reducing an intact protein to its secondary structure, a linear chain of amino acids, where it is enzymatically treated to cleave the amino acid chain at specific amino acid residues to produce a mixture of peptides. Individual peptide physicochemical properties (e.g., pKa, hydrophobicity, etc.) are determined by the accumulated properties of its constituent amino acids. As shown in FIGS. 1A-1D, amino acids can exhibit charged groups, polar groups, neutral groups (hydrophobic), as well as unique groups. Upon digestion, peptide-level analyses of protein-based therapeutics are commonly performed on LC-UV or LC-UV/MS platforms using reversed phase liquid chromatography (RPLC).

SUMMARY

Mobile phase additives such as formic acid (FA) and trifluoroacetic acid (TFA) are commonly used in RPLC to improve analyte retentivity and peak shape. However, FA and TFA do not necessarily complement each other as ion pairing reagents in peptide mapping workflows. Where FA produces favorable mass spectrum intensity compared to TFA in MS-based assays, as a weak ion pairing reagent, FA has increased baseline noise and broader peaks in UV-based assays compared to TFA. In addition, trace metal contamination in LC systems has been documented in the past as impacting recovery and separation performance of compounds exhibiting specific charge moieties such as phosphorylated groups. Trace metal contaminations have been linked to increased spectral adducts in analysis of oligonucleotides, which can negatively affect chromatographic separation.

The present technology solves the problems of the prior art by using a metal chelator as a mobile phase additive, particularly citric acid as a mobile phase additive. The use of citric acid as a mobile phase additive increases chromatographic performance (e.g., better resolution of peaks) and maintains chromatographic performance over an extended period of time (e.g., over 2-3 days or 64-100 consecutive injections). Prior attempts to use citric acid to enhance performance of LC/MS systems for phosphopeptide analysis have not changed the mobile phase (solvent) composition to avoid interference with chromatographic performance (Winter, et al., *Citrate Boosts the Performance of Phosphopeptide Analysis by UPLC-ESI-MS/MS*, J. of Proteome Research, 2009, 8, 418-424). However, the present technology changes the mobile phase by adding citric acid as an additive to the mobile phase, which is shown herein to enhance chromatographic performance of peptides and fatty acids.

In one aspect, the technology relates to a method of analyzing a sample that includes an analyte. The method includes injecting the sample that includes the analyte into a mobile phase comprising a metal chelator additive having a concentration between about 1 ppm to about 10 ppm. The method also includes separating the analyte using liquid chromatography and analyzing the analyte using a mass spectrometer, an ultra-violet detector, or a combination thereof. The method can include one or more of the embodiments described herein.

In some embodiments, the metal chelator additive is selected from the group consisting of citric acid, sodium citrate, isocitrate, ammonium citrate dibasic, and ammonium citrate tribasic. The metal chelator additive can be citric acid. In some embodiments, a concentration of citric acid in the mobile phase is from about 1 ppm to about 10 ppm. In some embodiments, the concentration of citric acid in the mobile phase is about 10 ppm. In some embodiments, the concentration of citric acid in the mobile phase is about 1 ppm.

In another aspect, the technology relates to a method of analyzing a sample that includes an intact protein for peptide mapping. The method includes reducing the intact protein in the sample to a linear chain of amino acids. The method also includes enzymatically treating the linear chain of amino acids to produce a mixture of peptides. The sample comprising the mixture of peptides is injected into a mobile phase comprising citric acid. The mixture of peptides is separated using reverse-phase liquid chromatography. The separated peptides are analyzed using a mass spectrometer, an ultra-violet detector, a fluorescence detector, or a combination thereof. The method can include one or more of the embodiments described herein.

In some embodiments, at least one peptide in the mixture of peptides comprises a charged amino acid residue. The at least one peptide in the mixture of peptides can have a net charge. In some embodiments, the net charge is negative. In some embodiments, the net charge is positive. Net charge for peptides refers to the sum of charges at a specific pH. From FIGS. 1A-1D, it can be seen that the side chains have different pKa's so depending on the pH of the mobile phase, the amino acids can have a positive or negative charge. The net charge sums the charge states up, for example, 5 positive charges and 6 negative charges would have a net "negative charge."

The protein can be a monoclonal antibody (mAb). In some embodiments, the protein is a synthetic protein or a recombinant protein.

In some embodiments, the amino acid is aspartic acid, glutamic acid, or iso-aspartic acid. The mixture of peptides can include PENNYK (SEQ ID NO:4) peptide and deamidated forms of the PENNYK (SEQ ID NO:4) peptide. The amino acid can be enzymatically treated with trypsin, Lys-C, Asp-N, or a combination thereof.

In some embodiments, chromatographic performance is maintained over a period of about 2 days to about 3 days with an average USP tailing value of about 0.95 to about 1.30. In some embodiments, chromatographic performance is maintained over about 48 consecutive injections with an average USP tailing value of about 0.95 to about 1.30. In some embodiments, the USP tailing value is between about 0.98 to about 1.20, or about 1.00 to about 1.10. In some embodiments, the USP tailing value is about 1.00.

In some embodiments, the mixture of peptides comprises a peptide and a deamidated species of the peptide.

A concentration of citric acid in the mobile phase can be from about 1 ppm to about 10 ppm. A concentration of citric acid in the mobile phase can be about 1 ppm. In some embodiments, a concentration of citric acid in the mobile phase is about 10 ppm.

The mobile phase can also include formic acid, acetic acid, water, acetonitrile, methanol, isopropanol, n-propanol, trifluoroacetic acid, difluoroacetic acid or a combination thereof.

In some embodiments, the method also includes passivating a reverse-phase chromatography column with citric acid prior to separating the mixture of peptides.

In another aspect, the technology relates to a method of analyzing a sample comprising a fatty acid. The method includes injecting the sample comprising the fatty acid into a mobile phase comprising citric acid. The method also includes separating the fatty acids using reverse-phase liquid chromatography. The separated fatty acids are separated using a mass spectrometer, an ultraviolet detector, or a combination thereof. The method can include one or more of the embodiments described herein.

In some embodiments, the fatty acid comprises lauric acid. A concentration of citric acid in the mobile phase can be from about 1 ppm to about 10 ppm.

In another aspect, the technology relates to a kit for analyzing a sample. The kit includes a liquid chromatography column, a vial comprising a citric acid mobile phase additive, and instructions for use of the citric acid mobile phase additive in a method for analyzing a sample comprising an analyte. The method includes adding the citric acid mobile phase additive to a mobile phase, injecting the sample comprising the analyte into the mobile phase comprising citric acid, separating the analyte using liquid chromatography, and analyzing the separated analyte using a mass spectrometer, an ultra-violet detector, or a combination thereof. The kit can include one or more of the embodiments described herein.

In some embodiments, the liquid chromatography column is a reverse-phase liquid chromatography column. The citric acid mobile phase additive can be added to the mobile at a concentration from about 1 ppm to about 10 ppm. The analyte can be a fatty acid. In some embodiments, analyte is an intact protein. In some embodiments, the concentration of citric acid is about 1 ppm. In some embodiments, the concentration of citric acid is about 10 ppm.

In some embodiments, the method also includes reducing the intact protein to a linear chain of amino acids and enzymatically treating the linear chain of amino acids to produce a mixture of peptides.

In another aspect, the technology relates to a kit for analyzing a sample. The kit includes a liquid chromatography column, a vial comprising a metal chelator mobile phase additive, and instructions for use of the citric acid mobile phase additive in a method for analyzing a sample comprising an analyte. The method includes adding the metal chelator mobile phase additive to a mobile phase to obtain a concentration of between about 1 ppm to about 10 ppm of the metal chelator mobile phase additive, injecting the sample comprising the analyte into the mobile phase comprising the metal chelator, separating the analyte using liquid chromatography, and analyzing the separated analyte using a mass spectrometer, an ultra-violet detector, a fluorescence detector, or a combination thereof. The kit can include one or more of the embodiments described herein.

In some embodiments, the metal chelator mobile phase additive is selected from the group consisting of citric acid, sodium citrate, isocitrate, ammonium citrate dibasic, ammonium citrate tribasic, and ammonium formate.

BRIEF DESCRIPTION OF THE DRAWINGS

The technology will be more fully understood from the following detailed description taken in conjunction with the accompanying drawings, in which:

FIG. 1A shows amino acids with electrically charged side chains.

FIG. 1B shows amino acids with polar uncharged side chains.

FIG. 1C shows amino acids that are special cases.

FIG. 1D shows amino acids with hydrophobic side chains.

FIG. 2A is an example of a peptide map showing all peptides that were ionized and detected via MS from the tryptic digest.

FIG. 2D lists the gradient and other chromatographic conditions used for the representative chromatograms of FIGS. 2A, 2B, and 2C, according to an illustrative embodiment of the technology.

FIG. 9A is an extracted ion chromatogram (XIC) of major peptide species eluting within the region of the PENNYK (SEQ ID NO:4) peptide (T37) shown with no chelator added into the mobile phase, according to an illustrative embodiment of the technology. Corresponding baseline spectrums at initial conditions were used to assess spectral contaminants and are shown in the inset figures.

FIG. 9B is an extracted ion chromatogram (XIC) of major peptide species eluting within the region of the PENNYK (SEQ ID NO:4) peptide (T37) shown with 1 ppm citric acid added into the mobile phase, according to an illustrative embodiment of the technology. Corresponding baseline spectrums at initial conditions were used to assess spectral contaminants and are shown in the inset figures.

FIG. 11D is a chromatogram showing the experimental (1140) and Gaussian (1145) fits for 1 ppm chelator at 60° C. for T14 (LC) VDNALQSGNSQESVTEQDSK (SEQ ID NO:3), according to an illustrative embodiment of the technology.

FIG. 11E is a chromatogram showing the experimental (1150) and Gaussian (1155) fits for 1 ppm chelator at 40° C. for T14 (LC) VDNALQSGNSQESVTEQDSK (SEQ ID NO:3), according to an illustrative embodiment of the technology.

FIG. 11F is a chromatogram showing the experimental (1160) and Gaussian (1165) fits for no chelator at 40° C. for T14 (LC) VDNALQSGNSQESVTEQDSK (SEQ ID NO:3), according to an illustrative embodiment of the technology.

FIG. 13A is a peptide map of a trypsin digest of the NIST mAb RM without a chelator present. The same method was used as that outlined with respect to FIG. 2.

FIG. 13B is a peptide map of a trypsin digest of the NIST mAb RM with a chelator present, according an illustrative embodiment of the technology. The same method was used as that outlined with respect to FIG. 2.

FIG. 15 shows the system conditions that were used in the testing of several different mobile phase additives as shown in FIGS. 16-21, according an illustrative embodiment of the technology.

FIG. 16A is a chromatogram of the PENNYK (SEQ ID NO:4) peptide and is deamidated species (inset) with 1 ppm citric acid mobile phase additive, according to an illustrative embodiment of the technology.

FIG. 16B is a chromatogram of the PENNYK (SEQ ID NO:4) peptide and is deamidated species (inset) with 1 ppm sodium citrate mobile phase additive, according to an illustrative embodiment of the technology.

FIG. 17A is a chromatogram of the PENNYK (SEQ ID NO:4) peptide and is deamidated species (inset) with 1 ppm citric acid mobile phase additive, according to an illustrative embodiment of the technology.

FIG. 17B is a chromatogram of the PENNYK (SEQ ID NO:4) peptide and is deamidated species (inset) with 1 ppm isocitrate mobile phase additive, according to an illustrative embodiment of the technology.

FIG. 18A is a chromatogram of the PENNYK (SEQ ID NO:4) peptide and is deamidated species (inset) with 1 ppm citric acid mobile phase additive, according to an illustrative embodiment of the technology.

FIG. 18B is a chromatogram of the PENNYK (SEQ ID NO:4) peptide and is deamidated species (inset) with 1 ppm ammonium citrate dibasic mobile phase additive, according to an illustrative embodiment of the technology.

FIG. 18C is a combined QDa MS scan of the PENNYK (SEQ ID NO:4) peptide with 1 ppm citric acid mobile phase additive (top spectrum) and a combined spectrum of the baseline chromatogram (bottom spectrum), according to an illustrative embodiment of the technology. Although the baseline spectrum is not noted in FIGS. 18A and 18B, the same time area was used for the baseline as was used with respect to FIGS. 16A and 16B.

FIG. 18D is a combined QDa MS scan of the PENNYK (SEQ ID NO:4) peptide with 1 ppm ammonium citrate dibasic mobile phase additive (top spectrum) and a combined spectrum of the baseline chromatogram (bottom spectrum), according to an illustrative embodiment of the technology. Although the baseline spectrum is not noted in FIGS. 18A and 18B, the same time area was used for the baseline as was used with respect to FIGS. 16A and 16B.

FIG. 19A is a chromatogram of the PENNYK (SEQ ID NO:4) peptide and is deamidated species (inset) with 1 ppm citric acid mobile phase additive, according to an illustrative embodiment of the technology.

FIG. 19B is a chromatogram of the PENNYK (SEQ ID NO:4) peptide and is deamidated species (inset) with 1 ppm ammonium citrate tribasic mobile phase additive, according to an illustrative embodiment of the technology.

FIG. 20C is a combined QDa MS scan of the PENNYK (SEQ ID NO:4) peptide with 1 ppm citric acid mobile phase additive (top spectrum) and a combined spectrum of the baseline chromatogram (bottom spectrum), according to an illustrative embodiment of the technology. Although the baseline spectrum is not noted in FIGS. 20A and 20B, the same time area was used for the baseline as was used with respect to FIGS. 16A and 16B.

FIG. 20D is a combined QDa MS scan of the PENNYK (SEQ ID NO:4) peptide with 1 ppm medronic acid mobile phase additive (top spectrum) and a combined spectrum of the baseline chromatogram (bottom spectrum), according to an illustrative embodiment of the technology. Although the baseline spectrum is not noted in FIGS. 20A and 20B, the same time area was used for the baseline as was used with respect to FIGS. 16A and 16B.

FIG. 21A is a chromatogram of the PENNYK (SEQ ID NO:4) peptide and is deamidated species (inset) with 1 ppm citric acid mobile phase additive, according to an illustrative embodiment of the technology.

FIG. 21B is a chromatogram of the PENNYK (SEQ ID NO:4) peptide and is deamidated species (inset) with 5 µM Agilent InfinityLab mobile phase additive, according to an illustrative embodiment of the technology.

DETAILED DESCRIPTION

Figure 1A:
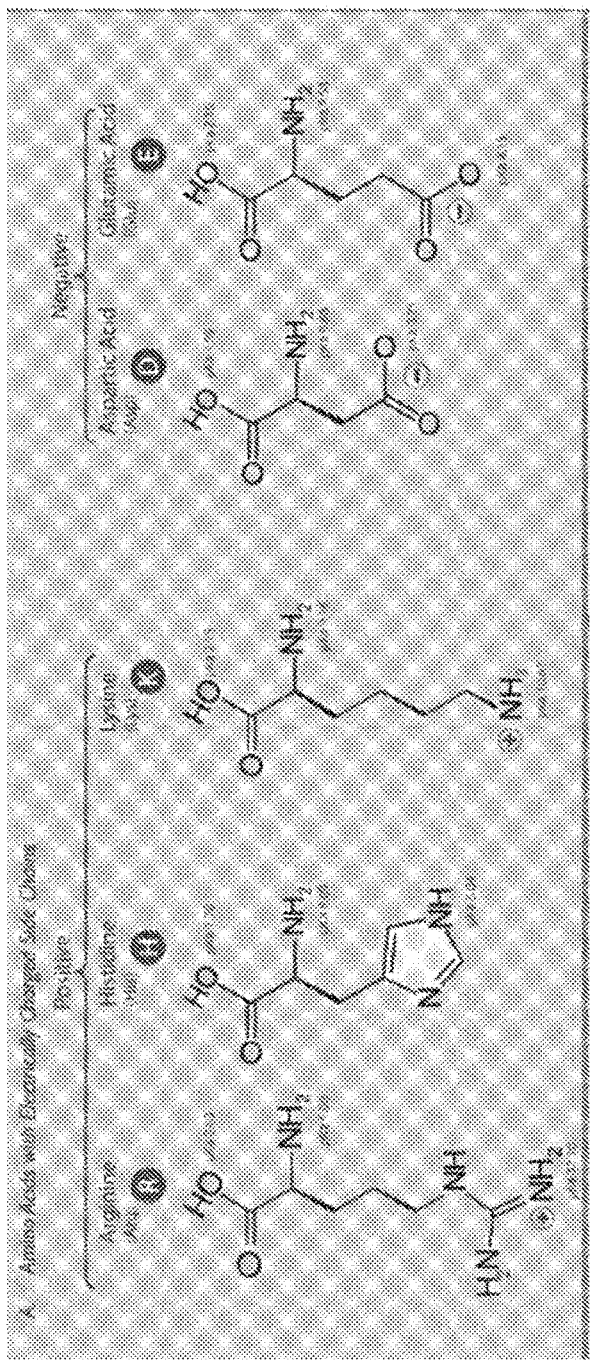
FIG. 1A shows that the physicochemical properties (e.g., pKa, hydrophobicity, etc.) of peptides are determined by the accumulated properties of its constituent amino acids.
Figure 1B:
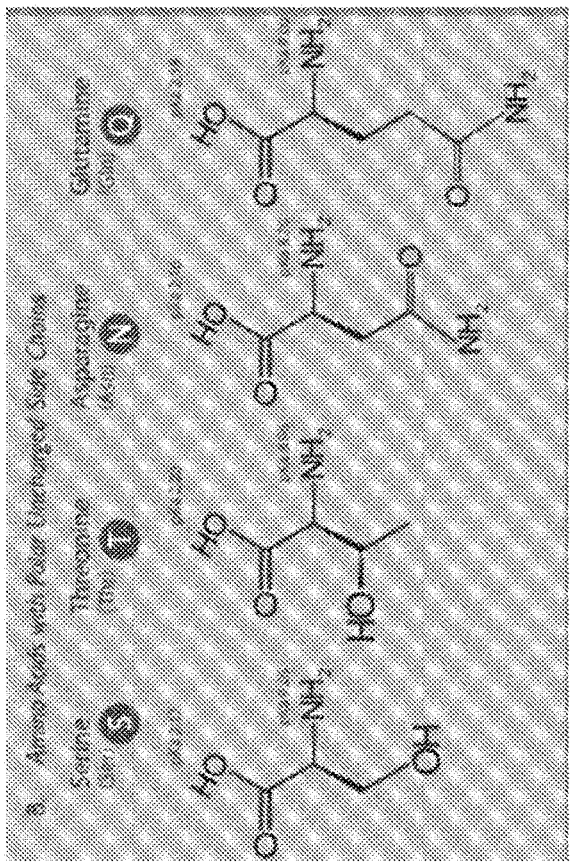
FIG. 1B shows that the physicochemical properties (e.g., pKa, hydrophobicity, etc.) of peptides are determined by the accumulated properties of its constituent amino acids.
Figure 1C:
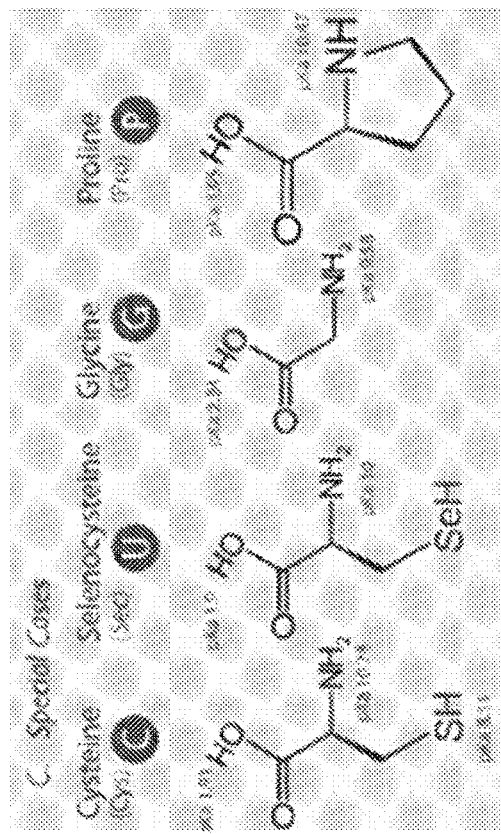
FIG. 1C shows that the physicochemical properties (e.g., pKa, hydrophobicity, etc.) of peptides are determined by the accumulated properties of its constituent amino acids.
Figure 1D:
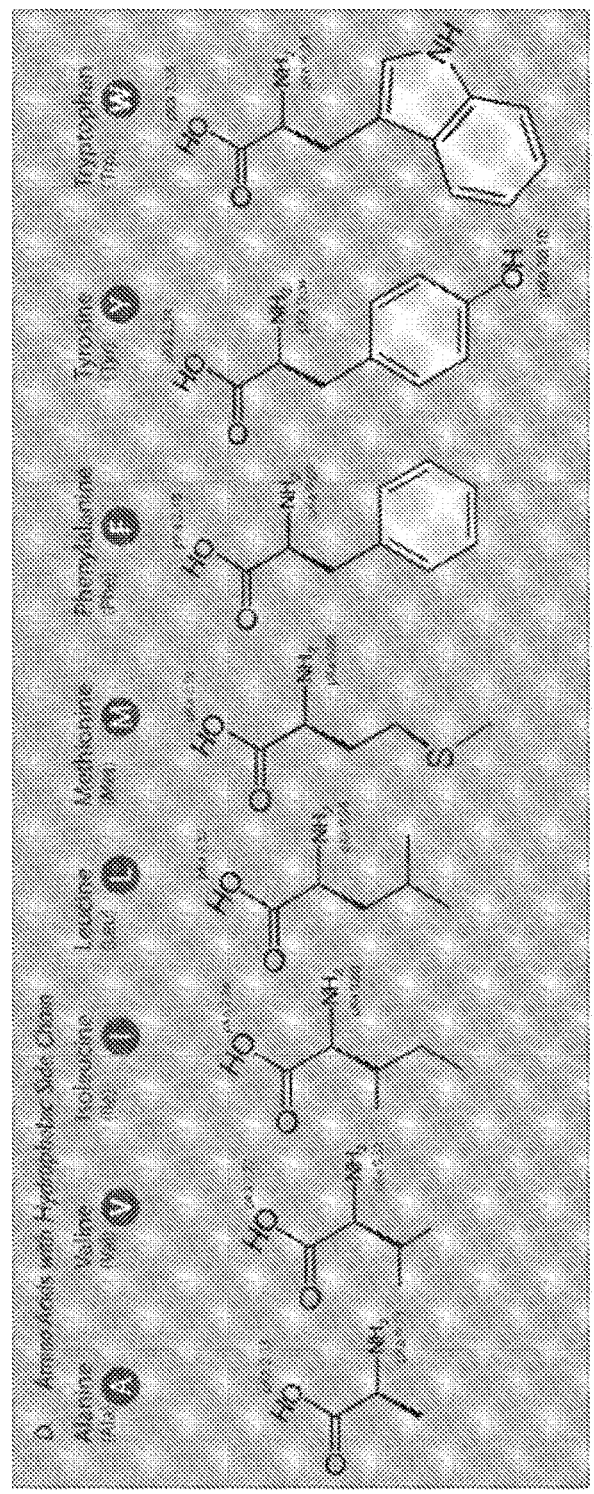
FIG. 1D shows that the physicochemical properties (e.g., pKa, hydrophobicity, etc.) of peptides are determined by the accumulated properties of its constituent amino acids.

Mobile phase additives such as formic acid (FA) and trifluoroacetic acid (TFA) are commonly used in RPLC to improve analyte retentivity and peak shape. However, FA and TFA do not necessarily complement each other as ion pairing reagents in peptide mapping workflows. Where FA produces favorable mass spectrum intensity compared to TFA in MS-based assays, as a weak ion pairing reagent, FA has increased baseline noise and broader peaks in UV-based assays compared to TFA. In addition to ionization efficiency, the ion pairing reagent chosen has a considerable effect on retentivity, separation efficiency, and chromatographic resolution, which can impact peak shape and width to varying degrees. Confounding the impact of ion-pairing reagent choice is the presence of non-specific interaction of protein and/or peptides with wetted surfaces of the analysis flow path which can impact chromatographic performance.

Trace metal contamination in LC systems has been documented in the past as impacting recovery and separation performance of compounds exhibiting specific charge moieties such as phosphorylated groups. More recently, trace metal contaminations have been linked to increased spectral adducts in analysis of oligonucleotides. Given this evidence, it is not without merit to reason peptides with charged moieties may also interact with trace metals which can negatively impact chromatographic performance.

Sources of trace metal contamination have been identified as impurity containing mobile phases, metal surfaces such as instrument tubing, and even metal containing column hardware such as frits and the column's housing itself. In these cases, metal impurities such are iron can leach out or desorb from the metal surfaces and embed themselves along the flow path in frits, filters, and even the stationary phase where upon they can negatively interact with the target analyte under investigation. This presents challenges when developing peptide mapping workflows where chromatographic resolution of impurities require methods that can deliver consistent and accurate measurements in a robust manner yet the entire flow path is at risk for trace metal contamination which can impede analysis.

Application of metal chelating agents such as EDTA or CDTA to "clean" LC systems is one approach to minimize trace metal contamination. However, these system washes tend to be long and tedious resulting in significant instrument down time. Engineering LC systems with inert material such as PEEK or low iron containing metal alloys is another approach, however, process complexity and material availability can increase costs and delay deployment of such systems. An alternative approach to mitigate metal contamination is to add trace metal chelating agents directly to mobile phases to act as a metal scavenger to solubilize and minimize contamination of wetted surfaces as well as act as a protecting group to any insoluble contaminant containing surface. While literature has shown the impact of such additives to small phosphorylated compounds with respect to recovery and to some degree chromatographic performance, little if any evidence exists regarding the potential application to biomolecules such as peptides. The objective of the current technology is to demonstrate the applicability of adding metal chelating agents to mobile phases as an additive to improve chromatographic performance of RPLC-based peptide separations.

The technology includes a method of analyzing a sample that includes an analyte. The technology includes injecting the sample into a mobile phase comprising a metal chelator additive that has a concentration between about 1 ppm to about 10 ppm. The concentration can be, for example, 1 ppm, 2 ppm, 3 ppm, 4 ppm, 5 ppm, 6 ppm, 7 ppm, 8 ppm, 9 ppm or 10 ppm. These values can be used to form a range, for example, between about 1 ppm to about 10 ppm or from about 2 ppm to about 5 ppm. The analyte is separated from the sample using liquid chromatography (LC). The separated analyte is analyzed using a mass spectrometer, an ultra-violet (UV) detector, or a combination thereof. The metal chelator can be citric acid at a concentration of about 1 ppm to about 10 ppm. The concentration of the citric acid can be, for example, 1 ppm, 2 ppm, 3 ppm, 4 ppm, 5 ppm, 6 ppm, 7 ppm, 8 ppm, 9 ppm or 10 ppm. These values can be used to form a range, for example, between about 1 ppm to about 10 ppm or from about 2 ppm to about 5 ppm. The metal chelator can also be sodium citrate, isocitrate, ammonium citrate dibasic, ammonium citrate tribasic, or a combination thereof.

As used herein, the term "about" means that the numerical value is approximate and small variations would not significantly affect the practice of the disclosed embodiments. Where a numerical limitation is used, unless indicated otherwise by context, "about" means the numerical value can vary by ±10% and remain within the scope of the disclosed embodiments.

The technology also includes a method of analyzing a sample comprising an intact protein for peptide mapping. The method includes reducing the intact protein in the sample to a linear chain of amino acids. The method also includes enzymatically treating the linear chain of amino acids to produce a mixture of peptides. The sample comprising the mixture of peptides is injected into a mobile phase comprising citric acid. The mixture of peptides is separated using RPLC. The separate peptides are analyzed using a mass spectrometer, an ultra-violet detector, a fluorescence detector, or a combination thereof. In some embodiments, sodium citrate, isocitrate, ammonium citrate dibasic, or ammonium citrate tribasic is used in addition to or instead of the citric acid.

At least one peptide in the mixture of peptides includes a charged amino acid residue or has a net charge. The net charge can be negative. The net charge can be positive. Table 1 shows the PENNYK (SEQ ID NO:4) peptide charge at different pH values. Formic acid pH is about 3.0 so the net charge is slightly positive. Without being bound by theory, the interaction with the metal ions is most likely occurring between the negative charges on the peptide chain. The protein can be synthetic or recombinant. The protein can be a monoclonal antibody (mAb). The amino acid can be aspartic acid, glutamic acid, or isoaspartic acid. The mixture of peptides can include a peptide and a deamidated species of that peptide. For example, the mixture of peptides can include a PENNYK (SEQ ID NO:4) peptide and deamidated forms of the PENNYK (SEQ ID NO:4) peptide (as discussed in detail below). The amino acid can be enzymatically treated with trypsin, Lys-C, Asp-N or a combination thereof. The amino acid can be enzymatically treated with other enzymes known to those of skill in the art.

TABLE 1

PENNYK (SEQ ID NO:4) Peptide Charge at Various pH values

| pH | Charge |
|---|---|
| 1.00 | 2.0 |
| 1.50 | 2.0 |
| 2.00 | 1.9 |
| 2.50 | 1.7 |
| 3.00 | 1.4 |
| 3.50 | 0.8 |
| 4.00 | −0.0 |
| 4.50 | −1.2 |
| 5.00 | −2.2 |
| 5.50 | −2.7 |
| 6.00 | −2.9 |
| 6.50 | −3.0 |
| 7.00 | −3.1 |
| 7.50 | −3.2 |
| 8.00 | −3.5 |
| 8.50 | −3.9 |

TABLE 1-continued

PENNYK (SEQ ID NO:4) Peptide Charge at Various pH values

| pH | Charge |
|---|---|
| 9.00 | −4.2 |
| 9.50 | −4.7 |
| 10.00 | −5.5 |

The USP tailing value can be about 0.95 to about 1.30 and can be maintained over a period of about two days to about three days. The USP tailing value can be maintained for about 1 day, 2 days, 3 days, 4 days, or 5 days. The USP tailing value can be maintained over about 48 consecutive injections. For example the USP tailing value can be maintained over between about 40 to about 100 consecutive injections. In some embodiments, the USP tailing value is between about 0.98 to about 1.20, or about 1.00 to about 1.10. In some embodiments, the USP tailing value is about 1.00.

The concentration of the citric acid can be, for example, 1 ppm, 2 ppm, 3 ppm, 4 ppm, 5 ppm, 6 ppm, 7 ppm, 8 ppm, 9 ppm or 10 ppm. These values can be used to form a range, for example, between about 1 ppm to about 10 ppm or from about 2 ppm to about 5 ppm. The mobile phase can also include formic acid, acetic acid, water, acetonitrile, methanol, isopropanol, n-propanol, or a combination thereof.

The method can also include passivating the RPLC column with citric acid prior to separating the mixture of peptides.

The methods described herein can also be used to separate an analyze fatty acids (e.g., lauric acid). The method can include injecting a sample comprising a fatty acid into a mobile phase that includes citric acid. The fatty acid can be separated using RPLC. The separated fatty acid can be analyzed using a mass spectrometer, an ultraviolet detector, a fluorescent detector, or a combination thereof.

The concentration of the citric acid can be, for example, 1 ppm, 2 ppm, 3 ppm, 4 ppm, 5 ppm, 6 ppm, 7 ppm, 8 ppm, 9 ppm or 10 ppm. These values can be used to form a range, for example, between about 1 ppm to about 10 ppm or from about 2 ppm to about 5 ppm. Other embodiments that are described with respect to the separation of peptides can also be used when separating fatty acids.

The technology described herein also includes kits. A kit can include a liquid chromatography column (e.g., a RPLC column) and a vial comprising a citric acid mobile phase additive. The kit also contains includes for use of the citric acid mobile phase additive in a method for analyzing a sample comprising an analyte (e.g., a peptide, PENNYK (SEQ ID NO:4) peptide, a fatty acid, lauric acid). The instructions can be any one of the methods described herein. The instructions can include the addition of the citric acid mobile phase additive to a mobile phase. The instructions can also include details on the specific concentrations of the citric acid mobile phase additive, for example, obtaining about 1 ppm to about 10 ppm citric acid mobile phase additive. The instructions can also state to inject the sample comprising the analyte into the mobile phase comprising citric acid. The analyte is separate using the liquid chromatography column (or an RPLC column) provided with the kit. The separated analyte can then be analyzed using a mass spectrometer, an ultra-violet detector or a combination thereof. The analyte to be analyzed with the kit can be a fatty acid, lauric acid, a protein, a peptide, the PENNYK (SEQ ID NO:4) peptide, an intact protein, a synthetic protein, a recombinant protein, or a combination thereof.

Wherein the analyte is a protein, an intact protein, a synthetic protein, or a recombinant protein, the method can also include reducing the intact protein to a linear chain of amino acids and enzymatically treating the linear chain of amino acids to produce a mixture of peptides.

As another example of a kit of the present technology, the kit can include a liquid chromatography column, a vial comprising a metal chelator mobile phase additive and instructions for the use of the metal chelator additive in any of the methods described herein. For example, the method can include adding the metal chelator mobile phase additive to a mobile phase to obtain a concentration of between about 1 ppm to about 10 ppm of the metal chelator mobile phase additive, injecting the sample having an analyte into the mobile phase with the metal chelator, separating the analyte using LC, and analyzing the separate analyte using a mass spectrometer, an ultra-violet detector, a fluorescence detector, or a combination thereof. The metal chelator additive can be citric acid. The metal chelator can also be sodium citrate, isocitrate, ammonium citrate dibasic, ammonium citrate tribasic, or ammonium formate.

Figure 2A:
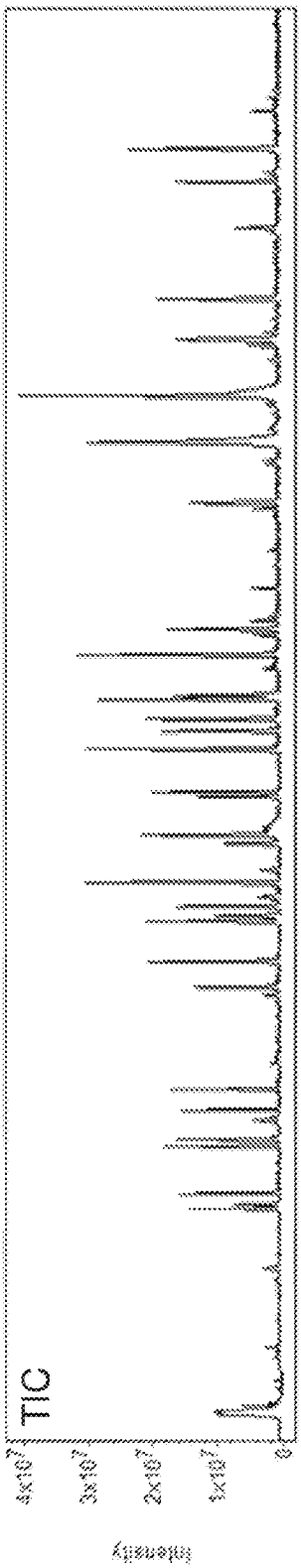
FIG. 2A is a representative total ion chromatogram (TIC) of to trypsin digest of the NIST mAb RM, according to an illustrative embodiment of the technology.
Figure 2B:
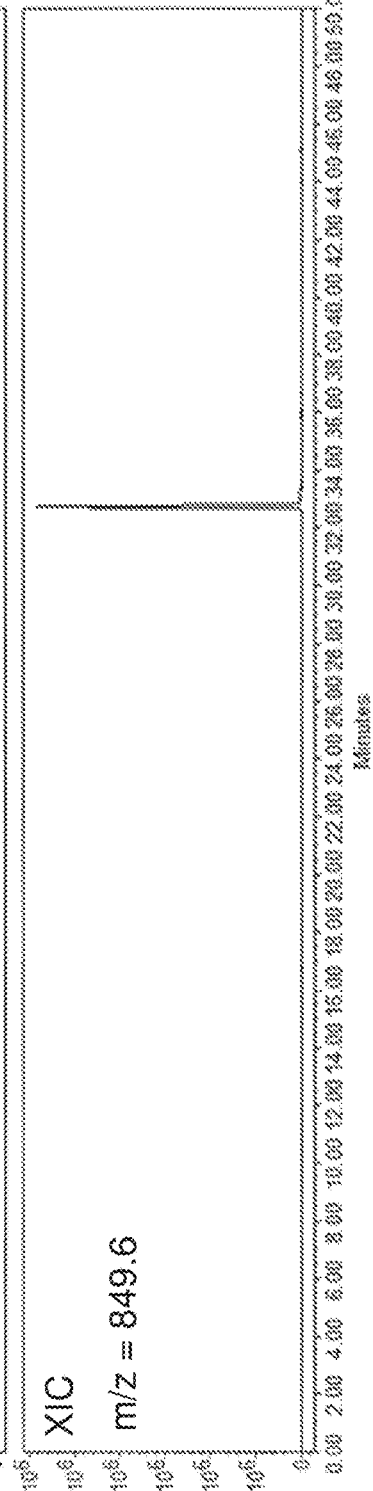
FIG. 2B is a representative extraction ion chromatograph (XIC) of the PENNYK (SEQ ID NO:4) peptide, according to an illustrative embodiment of the technology.
Figure 2C:
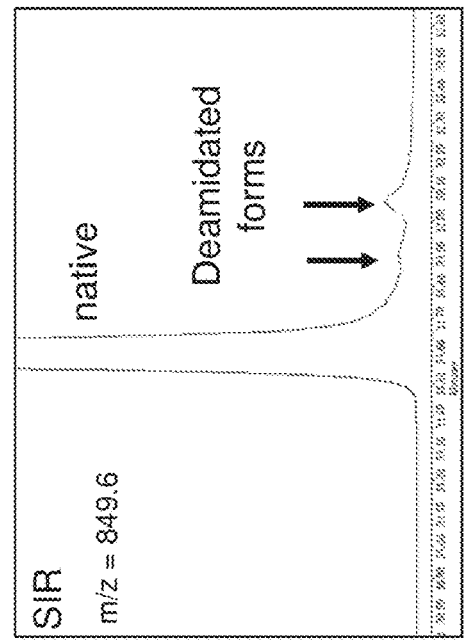
FIG. 2C is a representative single ion recordings (SIR) chromatogram of the PENNYK (SEQ ID NO:4) peptide showing that the PENNYK (SEQ ID NO:4) peptides native and deamidated forms closely elute as a critical pair using a modest gradient under formic acid conditions (see FIG. 2D), according to an illustrative embodiment of the technology.

For an initial study, identification of a representative peptide and associated figures of merit is necessary to evaluate the impact of the chelating agent on chromatographic performance. To this end, the peptide under investigation should be of importance to the target application landscape and contain charged amino acid residues that may interact with metal species. Deamidation of aspargine to aspartic acid and iso-aspartic acid is a common post-translational modification of monoclonal antibodies (mAbs). Due to its direct correlation to drug efficacy, deamidation has been recognized as a critical quality attribute (CQA) of mAb-based therapeutics. As a result, biopharmaceutical companies invest a significant amount of resource in the control and monitoring of impurities such as deamidation. Of the deamidated species monitored, the PENNYK (SEQ ID NO:4) peptide is of notable interest as it contains 7 hydrophobic amino acids and 4 charge bearing amino acids after enzymatic treatment of the intact mAb with trypsin. These features make its separation particularly challenging (See FIGS. 2A, 2B, and 2C). Using a RPLC-based separation, the PENNYK (SEQ ID NO:4) peptides native and deamidated forms closely elute as a critical pair using a modest gradient under formic acid conditions (see FIG. 2D). Peak tailing, as shown in the SIR trace of FIG. 2C, can impede accurate integration of the deamidated forms. For LC-based separations, an ideal peak is defined as being Gaussian with a tailing factor of 1.0 and a narrow peak width. For the initial investigation USP tailing factor at 5% will be used as a figure of merit to evaluate the impact of using chelating agents as a mobile phase additive in RPLC-based separations of peptides.

SEQ ID NO 1: G<u>FYPSD</u>IAVEWE<u>S</u>NGQPENNYK

The underlined portions of SEQ ID NO 1 are hydrophobic, the bold portions are charged, and the italics portions are anionic (note that some are charged and anionic denoted by being both bold and italics). The molecular formula is $C_{114}H_{158}N_{28}O_{39}$, the monoisotopic mass is 2543.12 Da, and the average mass is 2544.67 Da.

Regarding the figure of merit, in RPLC-based methods, peak tailing is generally accepted as a result of C-term contributions to overall chromatographic performance. The presence of electrostatic interaction of charged groups potentially can manifest itself as tailing as well as charge bearing peptides interact with trace metal contamination in the wetted flow path. For these reasons, USP Tailing Factor can be used as a figure of merit for the determining the impact of metal chelators on peptides (see EQ. 1)

$$T_f = \frac{W_{0.05}}{2F} \qquad \text{EQ. 1}$$

Figure 3:
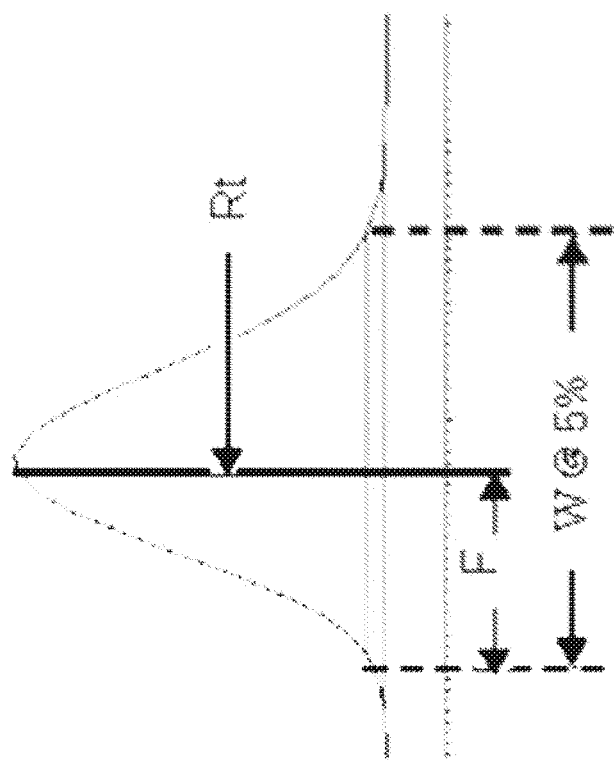
FIG. 3 is a graph depicting the variables used in the calculation of the figure of merit, according to an illustrative embodiment of the technology.

In EQ. 1, $T_f$ is the tailing factor, $W_{0.05}$ is the peak width at 5% of peak height, $R_t$ is the retention time, F is the time from width start point at 5% of peak height to retention time ($R_t$) (See FIG. 3). The tailing factor, $T_f$, establishes the maximum permissible asymmetry of the peak. For pharmaceutical purposes, $T_f$ is defined as the distance between the leading edge and tailing edge of the peak at a width of 5% of the peak height divided by twice the distance, F, between the peak maximum and the leading edge of the peak, at 5% of peak height. For a symmetrical peak, $T_f$ is 1.0, and the value of $T_f$ increases as tailing becomes more pronounced. When $T_f$ is less than 1.0, there is "fronting" of the peak, which can be related to mass load or potential overloading.

Figure 4B:
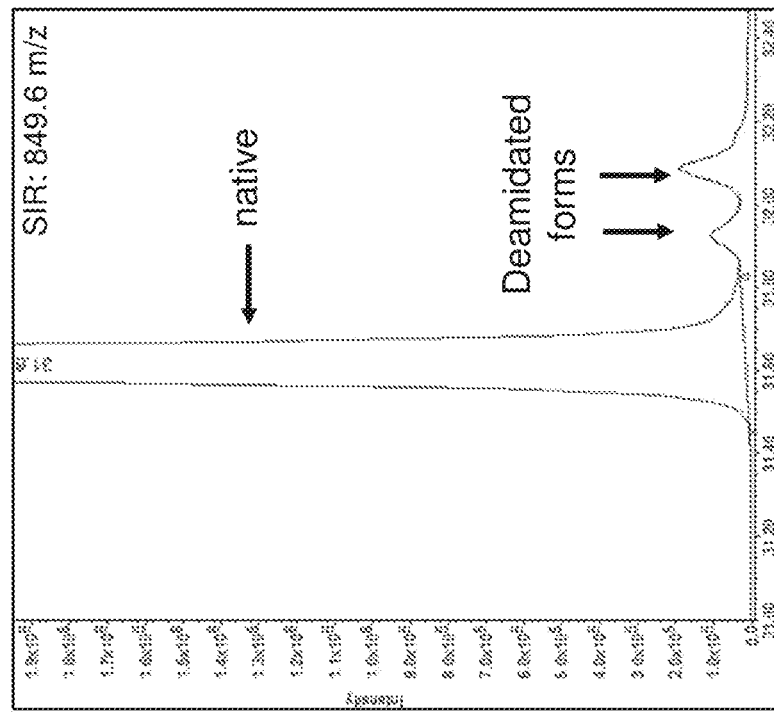
FIG. 4B is a chromatogram showing the baseline performance of a system with a RPLC/MS-based separation of the PENNYK (SEQ ID NO:4) peptide 12 hours after a cleaning procedure that incorporated a 30% phosphoric acid solution, according to an illustrative embodiment of the technology.
Figure 4A:
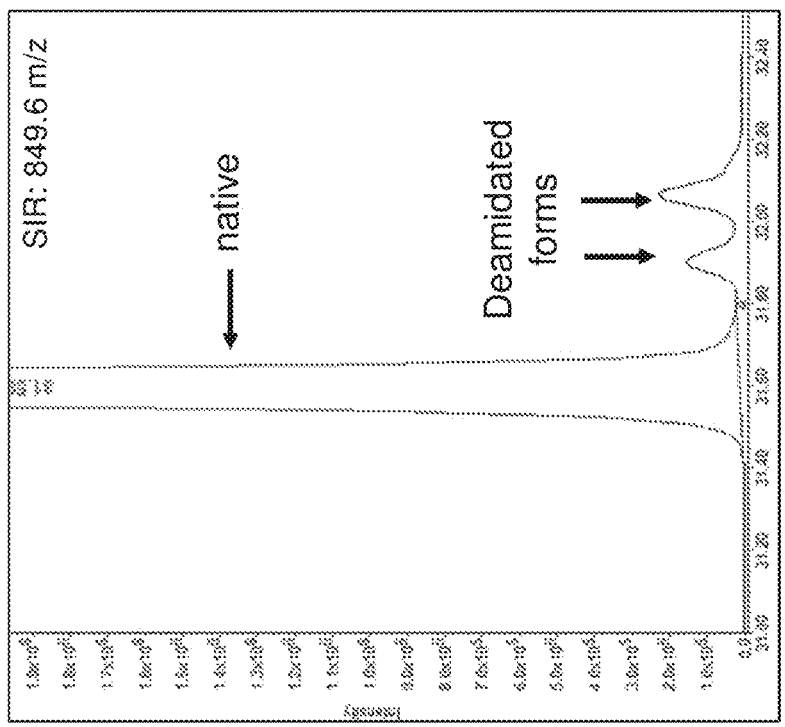
FIG. 4A is a chromatogram showing the baseline performance of a system with a RPLC/MS-based separation of the PENNYK (SEQ ID NO:4) peptide directly following a cleaning procedure that incorporated a 30% phosphoric acid solution, according to an illustrative embodiment of the technology.
Figure 4C:
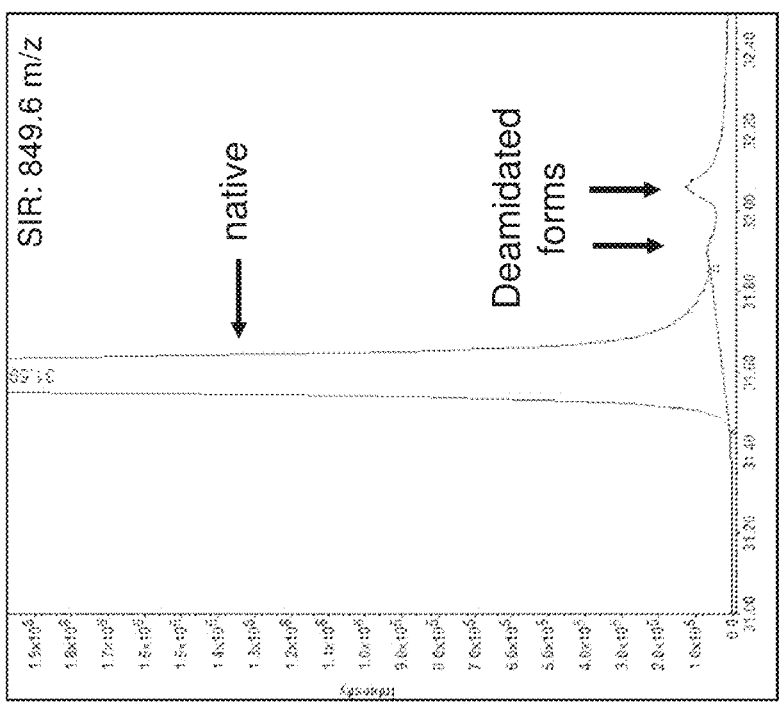
FIG. 4C is a chromatogram showing the baseline performance of a system with a RPLC/MS-based separation of the PENNYK (SEQ ID NO:4) peptide 24 hours after a cleaning procedure that incorporated a 30% phosphoric acid solution, according to an illustrative embodiment of the technology.
Figure 5A:
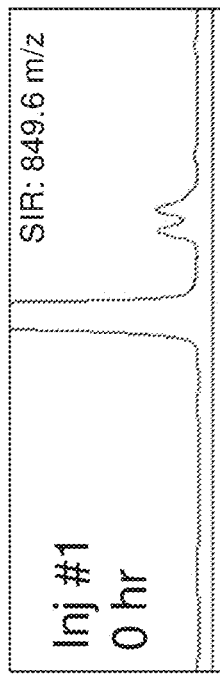
FIG. 5A is a chromatogram showing a separation using mobile phases that were prepared with the metal chelator citric acid at a concentration of 0.001%, at the initial injection, according to an illustrative embodiment of the technology.
Figure 5B:
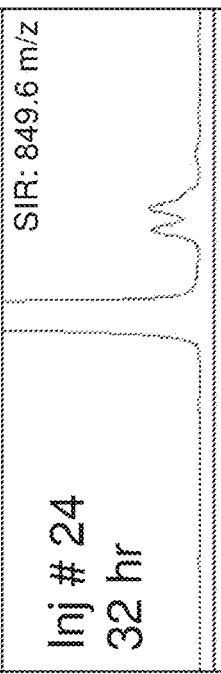
FIG. 5B is a chromatogram showing a separation using mobile phases that were prepared with the metal chelator citric acid at a concentration of 0.001%, at the $24^{th}$ injection at 32 hours, according to an illustrative embodiment of the technology.
Figure 5C:
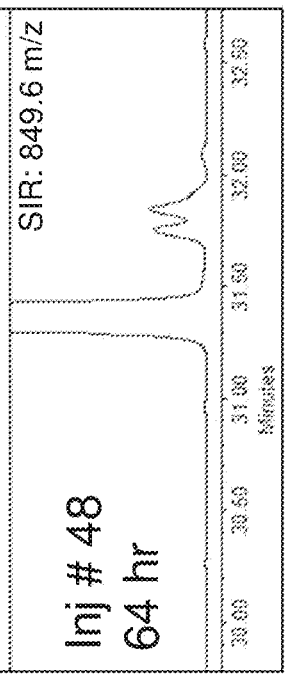
FIG. 5C is a chromatogram showing a separation using mobile phases that were prepared with the metal chelator citric acid at a concentration of 0.001%, at the $48^{th}$ injection at 64 hours, according to an illustrative embodiment of the technology.
Figure 5D:
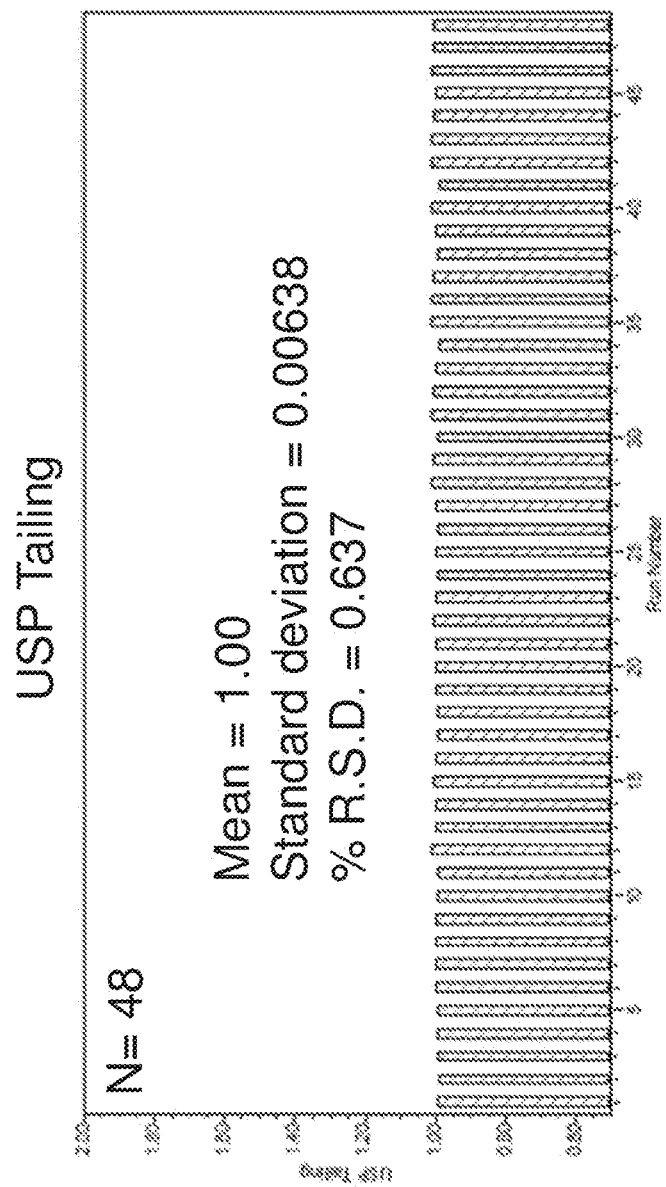
FIG. 5D is a graph showing the USP tailing value, according to an illustrative embodiment of the technology.

From previous work investigating adduct formation in oligonucleotide separations, it was found that an initial system wash using 30% phosphoric acid is able to reduce trace metal contamination in LC systems. Using this same protocol, the LC system was cleaned to determine baseline performance of the PENNYK (SEQ ID NO:4) peptide using an RPLC-based separation method. The protocol involves cleaning and passivating the LC/MS system prior to each experiment using a solution comprising 30% phosphoric acid v/v %. Acid was prepared using LC/MS grade water from stock reagents. The system modules that were cleaned and passivated including the BSM, AS-FTN and the CM-A with a stainless-steel union in place of a column. Flow was directed to waste after the union bypassing the TUV and mass detector. For each treatment, a 250 mL solution of the acid was prepared and allowed to flow through the LC/MS system at 1.0 mL/min for 250 minutes. Following the cleaning and passivation protocol, 1 L of LC/MS grade water was used to flush the system at a flow rate of 1 mL/min overnight or for at least 12 hours or until the eluent reached a pH of approximately 7.0. As shown in FIG. 4A, an RPLC-based method is able to resolve the native form of PENNYK (SEQ ID NO:4) from its deamidated forms with minimal tailing directly after leaning the system with the 30% phosphoric acid solution. However, chromatography performance was observed to deteriorate running the same method 12 hours (FIG. 4B) and 24 hours (FIG. 4C) later using the same sample and mobile phases based on USP tailing factor as well as visual assessment of resolution between the native and deamidated peptide forms. This suggests that a build-up of trace metal contamination is occurring and negatively impacting the methods ability to resolve the native and deamidated forms of the PENNYK (SEQ ID NO:4) peptide. To maintain chromatographic performance, mobile phases were prepared with the metal chelator citric acid as a concentration of 0.01%. Using the same method, 48 consecutive injections were made of a form for tryptic digest of the NIST mAb reference material. As shown in FIGS. 5A-5C, chromatographic performance was maintained for the PENNYK (SEQ ID NO:4) peptide over a 64 hour period with an average USP tailing value of 1.00 (FIG. 5D).

This demonstrates that chelating agents as mobile phase additives can increase and maintain chromatographic performance of critical species over an extended time period.

Example 1—PENNYK (SEQ ID NO:4) Peptide

Metal-ion mediated adsorption in liquid chromatography has been identified as a contributing factor in poor peak shape, tailing, and diminished recovery of compounds prone to cation exchange-like interaction with metal-based activity sites. Peptides that exhibit negative charge bearing amino acids such as aspartic acid, and glutamic acid are particularly sensitive to metal-ion mediated adsorption in RPLC/MS-based separations when using weak acids (e.g. formic acid) as mobile phase additives. Citric acid and medronic acid as metal complexing mobile phase additives were evaluated for their ability to mitigate metal-ion mediated adsorption in RPLC/MS-based peptide mapping assays. In this example, chromatographic performance was stabilized with peak tailing for peptides of interest reduced by as much as 40% in the presence of a chelator at a mobile phase concentration of 1 ppm. Performance gains were observed to be stable over a 67-hour time study with an average USP tailing factor of 1.00, % RSD=0.64. The stabilizing effect of the chelator improved peptide mapping assay robustness with relative peak areas for target impurities calculated at 2.32% (% R.S.D.=2.23) and 2.57% (% R.S.D.=3.97). This example demonstrates that chelators as mobile phase additives offer a means to improve chromatographic performance for biomolecules sensitive to metal-ion mediated adsorption under formic acid-based RPLC conditions.

Metal-ion mediated adsorption has been established as a contributing factor in poor peak shape, tailing, and diminished recovery of compounds prone to charge-based interactions in LC-based assays. Without being bound by theory, the proposed mechanism is that trace mobile phase contaminants in the form of metal impurities are adsorbed by active sites within the wetted flow path or column where upon they exhibit cation exchange characteristics toward solute molecules bearing negative charges. The strong binding characteristics exhibited by these high energy activity sites result in peak tailing and diminished recovery where desorption of adsorbed solute molecules, if present, occurs towards the rear zone of an eluting band. This immobilized metal ion affinity chromatography (IMAC)-like phenomenon has proven to be particularly problematic in the separation and recovery of phosphorylated compounds where the intrinsic chelating property of the phosphate group enhances the metal-ion binding characteristics.

The incorporation of mobile phase additives in chromatography is a well-established strategy in the suppression of adsorption characteristics of high energy activity sites. In the case of metal-ion mediated adsorption, early work with MALDI-MS-based techniques demonstrated improved recovery of phosphorylated compounds with the addition of diammonium citrate or phosphoric acid to the matrix. The benefit of metal complexing agents to improve phosphorylated peptide recovery was further studied in LC-ESI-MS analyses using EDTA as well as phosphoric acid as sample additives. Improvement to these techniques was demonstrated by Winter et al. using a more MS compatible chelating agent in the form of citrate to overcome clogging of the ESI spray needle under RPLC conditions when EDTA is used. (D. Winter, J. Seidler, Y. Ziv, Y. Shiloh, W. D. Lehmann, *Citrate boosts the performance of phosphopeptide analysis by UPLC-ESI-MS/MS*, Journal of proteome research, 8 (2009) 418-424.) Further investigation by Siedler et al. demonstrated performance gains using metal complexing agents as sample additives could be realized across various LC/MS configurations. (J. Seidler, N. Zinn, E. Haaf, M. E. Boehm, D. Winter, A. Schlosser, W. D. Lehmann, *Metal ion-mobilizing additives for comprehensive detection of femtomole amounts of phosphopeptides by reversed phase LC-MS*, Amino acids, 41 (2011) 311-320.)

More recently, Hsiao et al. investigated the recovery and peak shape of anionic and phosphorylated compounds under HILIC conditions in the presence of metal ion complexing agents. (J. J. Hsiao, O. G. Potter, T. W. Chu, H. Yin, *Improved LC/MS Methods for the Analysis of Metal-Sensitive Analytes Using Medronic Acid as a Mobile Phase Additive*, Analytical chemistry, 90 (2018) 9457-9464.) Of notable interest was the finding that direct addition of methylenediphosphonic acid (medronic acid) to the mobile phase did not yield significant ion-suppression or residual LC adsorption in comparison to more traditional chelating agents such as EDTA. With the potential to introduce metal impurities during the execution of experiments due to their universal presence at trace levels in make-up solvents, reagents, and LC equipment, direct approaches such as this are more appealing in the development of robust LC-based assays where tailing and poor peak shape of anionic or phosphorylated compounds can impact assay sensitivity and accuracy as in the case of therapeutic proteins.

Peptide-based analyses are one of the primary analytical methods regularly performed throughout the lifecycle of therapeutic proteins. It has proven to be an invaluable tool in the characterization and quality control of protein-based therapeutics to elucidate structural information and assess protein modifications. More recently, MS-based peptide mapping has been depoloyed in manufacturing environments to improve productivity and data quality by effectively monitoring multiple potential critical quality attributes (pCQAs) simultaneously. As part of their composition, peptides inherently will contain negative charge bearing amino acids in the form of aspartic acid, and glutamic acid which can potentially be impacted by metal-ion mediated adsorption. Interestingly, a search of the literature indicated limited information can be found in the evaluation of metal complexing agents and their impact on peptides containing these charges motifs. This is not a surprising revelation considering ion-pairing agents such as trifluoracetic acid (TFA) are well established as mobile phase additives capable of suppressing adsorption artifacts to acceptable levels in RPLC-based peptide separations. However, with an increasing number of MS-based methods being implemented in the development and manufacturing of therapeutic biologics with weaker mobile phase additives such as formic acid (FA) being used in favor of sensitivity over chromatographic performance, there is concern for metal-ion mediated adsorption to impact assay robustness and performance.

The objective of this example is to evaluate the impact of metal complexing agents on peptides containing negative charge bearing residues (e.g. aspartic acid and glutamic acid) under RPLC-MS conditions. Chromatographic performance in terms of peak tailing and MS-response will be used as metrics to assess the results and discuss optimal strategies in reducing metal-ion mediated adsorption of non-phosphorylated anionic peptides.

Materials and Methods

Materials

NIST monoclonal antibody reference material 8671 was purchased from the National Institute of Standards and Technology (Gaithersburg, Md.) and stored at −80° C. prior to use. Tris-hydrochloride (Tris-HCl), guanidine-hydrochloride, dithiothreitol (DTT), Iodoacetamide (IAA), citric acid (≥99.5%), sodium citrate (Neat), ammonium citrate dibasic (≥99.0%), ammonium citrate tribasic (≥97%), DL-isocitric acid trisodium salt hydrate (≥93%), and ammonium formate (MS-grade) were purchased from Sigma-Aldrich (St. Louis, Mo.) and used as received. InfinityLab® Deactivator Additive (medronic acid) was purchased from Agilent Scientific Instruments (Santa Clara, Calif.) and used as per manufacturer instructions. Sequence grade modified trypsin was purchased from Promega (Madison, Wis.) and stored at −20° C. prior to use. LC/MS grade water, acetonitrile, and nitric acid were purchased from Honeywell (Charlotte, N.C.). LC/MS grade formic acid and O-Phosphoric Acid (85%) were purchased from Fisher Scientific (Hampton, N.H.). Bio-Rad® Micro-P6 Spin Columns were purchased from Bio-Rad Laboratories, Inc. (Hercules, Calif.) and stored at 4° C.

Sample Preparation

To control variability throughout the example, attention was given to sample selection, preparation, and data acquisition. A commercially available mAb standard (NIST RM 8671) was enzymatically treated with a protocol adapted from Ren et al. (*An improved Trypsin Digestion Method Minimizes Digesterion-Induced Modifications on Proteins*, Analytical Biochemistry, 392 (2009) 12-21) to reduce digestion artifacts. Briefly, intact mAb was digested with sequence grade trypsin using the following protocol. Stock solutions were prepared with LC/MS grade water were applicable. 20 μL of NIST mAb at 10 mg/mL was added to 60 μL of a denaturing buffer comprised of 0.1 M Tris-HCl (pH 7.5) and 8.25 M guanidine. To this solution 2.5 μl of DTT prepared in 0.1 M Tris-HCl (pH 7.5) was added at a concentration of 400 mM. The sample was incubated at 37° C. for 60 minutes in a MJ Research® PTC-100 thermal cycler (commercially available from MJ Research, Inc., Waltham, Mass.). Following incubation, 5 μL of 400 mM IAA prepared in 0.1 M Tris-HCl (pH 7.5) was added to the mixture followed by incubation for 45 minutes at room temperature in the dark. A Micro-P6 Spin Column (commercially available from Bio-Rad Laboratories, Inc., Hercules, Calif.) was prepared for sample desalting by washing with 500 μL of 0.1 M Tris-HCl (pH 7.5) buffer loaded on to the column and centrifuged into a waste vial at 1000 g for 1 minute using an Eppendorf® 5415 R Centrifuge (commercially available from Eppendorf AG, Hauppauge, N.Y.). This step was repeated for a total of 4 wash cycles. The sample was then loaded on to the center of the column bed and centrifuged at 1000 g for 4 minutes into a collection vial. Following desalting, 10 μL of 1 mg/mL trypsin prepared in manufacturer provided resuspension buffer was added to the sample at an enzyme to substrate ratio of 1:20. This mixture was incubated at 37° C. for 60 minutes. Following incubation, the digest was diluted in a 1:1 ratio with LC/MS grade water containing 0.1% formic acid. An injection volume of 10 μL was used for all analyses. To minimize sample degradation, samples were homogenized as a master pool and aliquoted into ppendorf LoBind® tubes (commercially available from Eppendorf AG, Hauppauge, N.Y.) and stored at −80° C. after enzymatic digestion prior to use.

LC/MS System Configuration

A Waters® ACQUITY® I-Class PLUS series LC instrument (commercially available from Waters Technologies Corporation, Milford, Mass.) was used for data acquisition to minimize system dispersion and to take advantage of the impact of gradient accuracy on chromatographic performance. The system was configured with a binary solvent manager (BSM) equipped with a 380 μL mixer (PN 205000705), flow through needle sample manager (SM-FTN), and column manager (CM-A). A tunable ultra-violet detector (TUV) equipped with a 10 mm analytical flow cell was used to acquire optical data at a wavelength of 214 nm. An ACQUITY® QDa® single quadrupole mass detector (commercially available from Waters Technologies Corporation, Milford, Mass.) was configured in-line post TUV to facilitate monitoring of critical peptide species. Reversed phase separations were performed on a Waters® ACQUITY® UPLC® CSH C18 column (1.7 μm, 2.1×100 mm) at 60° C. (commercially available from Waters Technologies Corporation, Milford, Mass.). A 60-minute gradient to 35% B was applied after an initial isocratic hold at 1% B for 5 minutes. The column was then cleaned by ramping the % B composition to 70% over 3 minutes and held at 70% for an additional 2 minutes. Column equilibration was then performed for 6 minutes after returning to initial conditions over 1 minute. All gradients were performed at flow rate of 0.200 ml/min with a total run time of 87 minutes. Mobile phases were prepared with LC/MS grade water (MP A) and acetonitrile (MP B) with 0.1% FA v/v. Metal complexing agent's citric acid and medronic acid were prepared in both mobile phases at 1 ppm or 5 μM, respectively. To ensure chelator solubility, mobile phases were prepared with 3% B in MP A and 3% A in MP B. MS quadrupole data was acquired at a sampling rate of 2 Hz in positive mode using a full scan range of 450-1250 m/z and single-ion recording at 849.2 m/z and 849.6 m/z to monitor the $[M+3H]^{+3}$ charge state of the native and deamidated forms of peptide T37(HC) of the NIST RM, respectively. Cone voltage, capillary voltage, and probe temperature were set at 10 V, 1.5 kV, and 600° C., respectively.

System Cleaning and Passivation

The LC/MS system was cleaned and passivated prior to each experiment using a solution of 30% (v/v %) phosphoric acid prepared with LC/MS grade water from stock reagents. The system modules that were cleaned and passivated included the BSM, AS-FTN, and the CM-A with a stainless-steel union in place of a column. Flow was directed to waste after the union bypassing the TUV and mass detector. For each treatment, a 250 mL solution of the phosphoric acid solution was prepared at the required concentration and allowed to flow through the LC/MS system at 1.0 mL/min for 250 minutes. Following the cleaning and passivation protocol, 1 L of LC/MS grade water was used to flush the system at a flow rate of 1 mL/min overnight or for at least 12 hours or until the eluent reached a pH of approximately 7.0. pH was determined by collecting approximately 10 mL of eluent in a plastic conical tube and measured using a Fisher Scientific Acument XL250 pH/mV/ISE Meter (Pittsburgh, Pa.).

Results and Discussion

For this example, identification of a representative peptide is necessary to evaluate the impact of the chelating agents on chromatographic performance. To this end the peptide under investigation should be of importance to the target application and contain charged amino acid residues that may interact with metal ions. Deamidation of asparagine to aspartic acid and iso-aspartic acid is a common post-translational modification of monoclonal antibodies (mAbs) that has been correlated to drug efficacy. As a result, biopharmaceutical companies invest a significant amount of resources in the control and monitoring of impurities such as deamidation. Of the deamidated species monitored, the PENNYK (SEQ ID NO:4) peptide (SEQ ID NO 1) is of notable interest as it contains 7 hydrophobic amino acids and 4 negative charge bearing amino acids after enzymatic treatment of the intact mAb with trypsin making it an ideal candidate for metal-ion mediated adsorption. Furthermore, the PENNYK (SEQ ID NO:4) sequence is in the constant region of the Fc domain in all humanized mAbs increasing its relevancy as a peptide routinely monitored as a critical quality attribute throughout the biopharmaceutical industry.

Prior to evaluation of metal complexing agents, establishing baseline system performance was necessary to facilitate comparison of results. From previous work it was observed that a 30% phosphoric acid solution was capable of displacing trace metal impurities adsorbed throughout the wetted flow path surfaces. Following a similar procedure, a phosphoric acid solution as used to clean the system fluidic path. After neutralizing the system, a series of 10 injections of mAb digest were made with 4 blank injections occurring between protein injections using conventional RPLC mobile phases ($H_2O$:MeCN, 0.1% FA) commonly encountered in RPLC/MS peptide mapping assays.

Figure 6A:
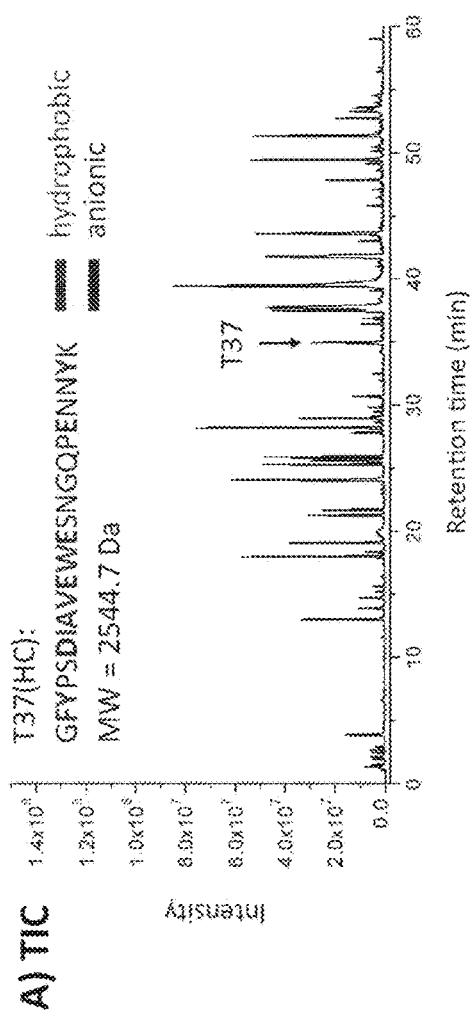
FIG. 6A is a chromatogram of a RPLC/MS-based separation of a trypsin-digested NIST mAb with the "PENNYK" (SEQ ID NO:4) peptide peak identified as a peptide of interest containing anionic residues, according to an illustrative embodiment of the technology.
Figure 6B:
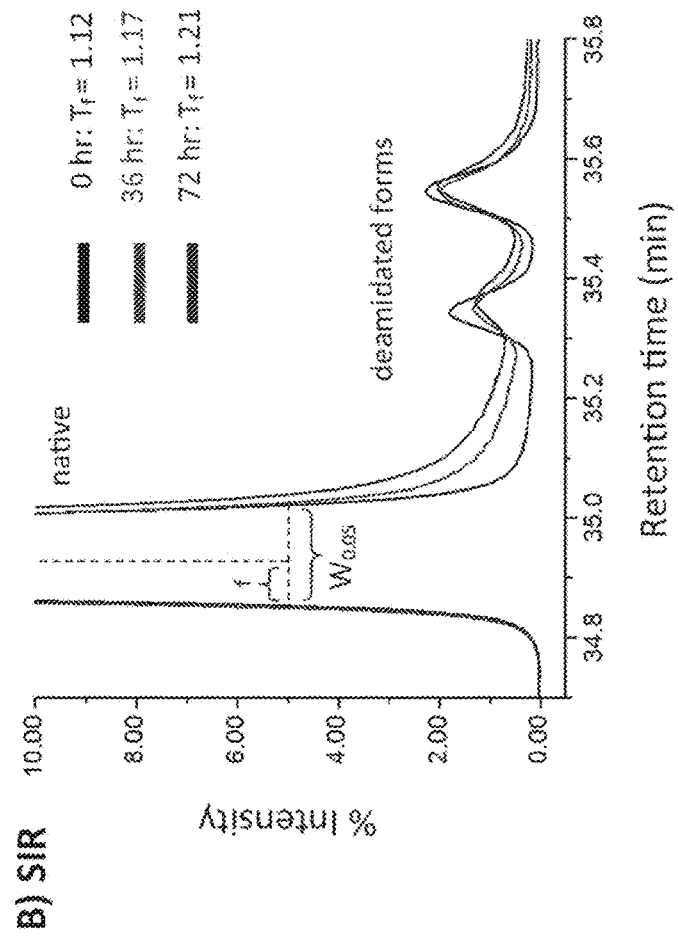
FIG. 6B is a single ion recordings (SIR) was used to monitor USP tailing factor of the PENNYK (SEQ ID NO:4) peptide and associated impurities at Woos over 72-hours using mobile phases comprised of $H_2O$:MeCN, 0.1% FA v/v. SIR overlays were time-aligned to facilitate comparison, according to an illustrative embodiment of the technology.

As noted in FIG. 6A, preliminary characterization of the native PENNYK (SEQ ID NO:4) peptide (T37) using an RPLC-based separation of the enzymatically treated NIST mAb reference material shows the PENNYK (SEQ ID NO:4) peptide eluting approximately in the middle of the 60-minute separation gradient with a retention time of 34.9 minutes. Due to the peak density of the chromatogram and closely eluting nature of the impurities, single ion recording (SIR) was used to monitor the profile of the native and deamidated forms as shown in FIG. 6B. USP tailing factor ($T_f=W_{0.05}/2f$) at 5% peak width was used to evaluate tailing of the PENNYK (SEQ ID NO:4) over the course of the injection series. Initial chromatographic performance (0 hr) was observed to be acceptable after the phosphoric acid wash with tailing of the native peak calculated at 1.12. However, tailing was observed to increase over 72 hours of continuous instrument use with a calculated tailing factor of 1.21. Traditionally, tailing values below 1.2 are generally viewed as acceptable in terms of chromatographic performance, however as shown in the chromatogram, the increased tailing can significantly impact the profile and integration of closely eluting low abundant peaks. In this injection series the leading impurity peak at 35.35 minutes exhibited a 12% decrease in relative area from 1.58% to 1.40% whereas the trailing impurity peak at 35.55 minutes exhibited a 25% increase from 2.20% to 2.76% over a 72-hour period. While subtle, these observations demonstrate that closely eluting low abundant impurities are more prone to exhibit increased variability in the presence of a relatively low degree of tailing, circumvention of which is impractical due to increased tailing as the trailing peak edge approaches the baseline.

Figure 7:
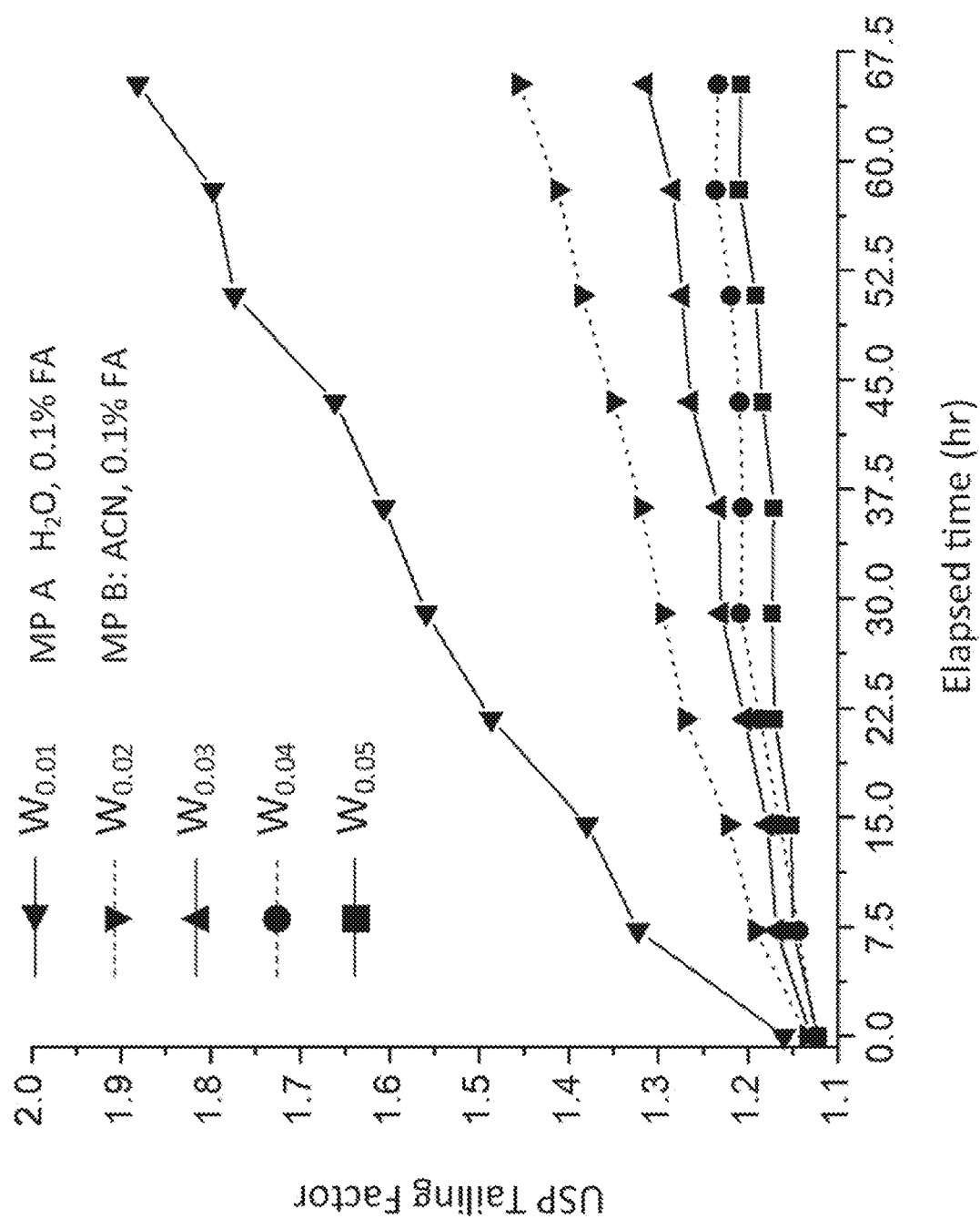
FIG. 7 is a graph showing tailing factors at and below $W_{0.05}$ were plotted at 7.5 hr intervals to monitor deterioration rates in chromatographic performance using mobile phases comprised of $H_2O$:MeCN, 0.1% FA v/v, according to an illustrative embodiment of the technology. Tailing factors were observed to have exponential-like behavior as peak widths approached baseline.

As shown in FIG. 7, the tailing factor at lower peak widths exhibits an exponential-like behavior making shallower gradients at the expense of longer run times and sensitivity a moot point. Upon closer inspection of FIG. 7, the observed deterioration of chromatographic performance over time suggests that the cause of tailing is being introduced in the form of a contaminant with adsorption characteristics rather than as a pre-existing condition given the system performs acceptably immediately following a cleaning protocol using phosphoric acid. In our previous study it was observed that metal adduct species such as $Na^+$ and $K^+$ were capable of adsorption onto metal surfaces within the LC fluidic path. However, the likelihood the activity sites are associated with $Na^+$ and $K^+$ is negligible considering it was shown acidic LC conditions induced by formic acid were sufficient in displacing weakly adsorbed metal ions such as Na and $K^+$. If metal-ion mediated adsorption is the cause of tailing, these observations would suggest a metal ion with stronger adsorption characteristics such as Fe II/III may be present in the wetted flow path as an adsorption site and contributing to the observed deterioration in chromatographic performance of the PENNYK (SEQ ID NO:4) peptide analogous to observations made by Seidler et al. (*Metal Ion-Mobilizing Additives for Comprehensive Detection of Femtomole Amounts of Phosphopeptides by Reversed Phase LC-MS*, Amino acids, 41 (2011) 311-320). Moving forward with this notion, a mitigation strategy employing metal complexing agents was explored.

Figure 8A:
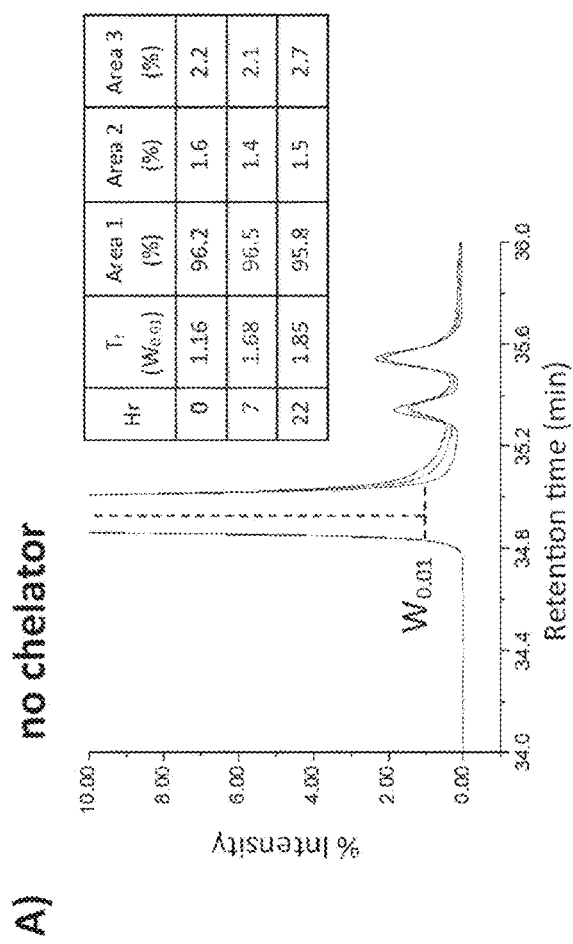
FIG. 8A is a chromatogram showing PENNYK (SEQ ID NO:4) peptide SIR overlays of 3 injections over time with no chelator added into to the mobile phase, according to an illustrative embodiment of the technology. Tailing factor and relative peak area calculations are reported in the table insets. SIR overlays were time-aligned to facilitate comparison.
Figure 8B:
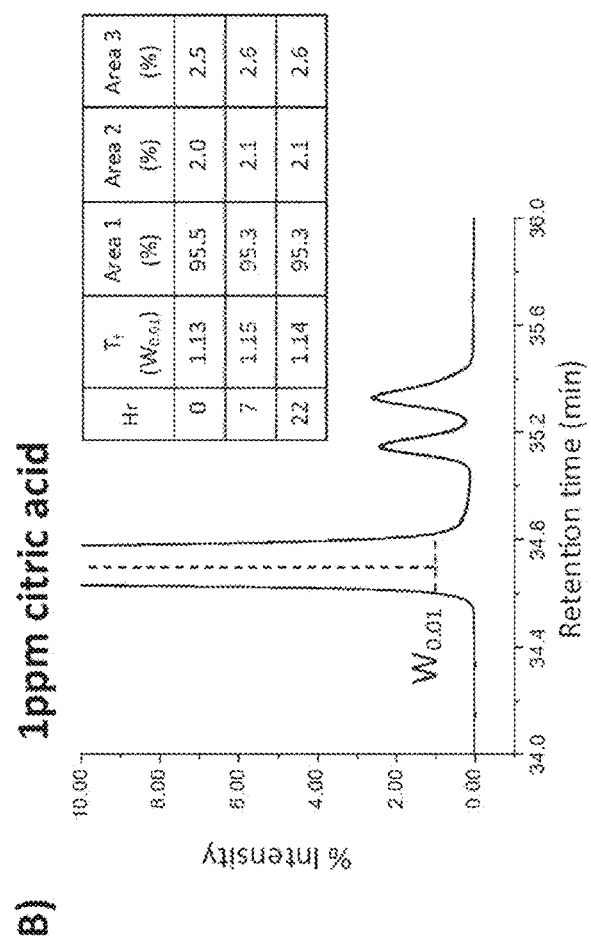
FIG. 8B is a chromatogram showing PENNYK (SEQ ID NO:4) peptide SIR overlays of 3 injections over time with 1 ppm citric acid added into to the mobile phase, according to an illustrative embodiment of the technology. Tailing factor and relative peak area calculations are reported in the table insets. SIR overlays were time-aligned to facilitate comparison.
Figure 8C:
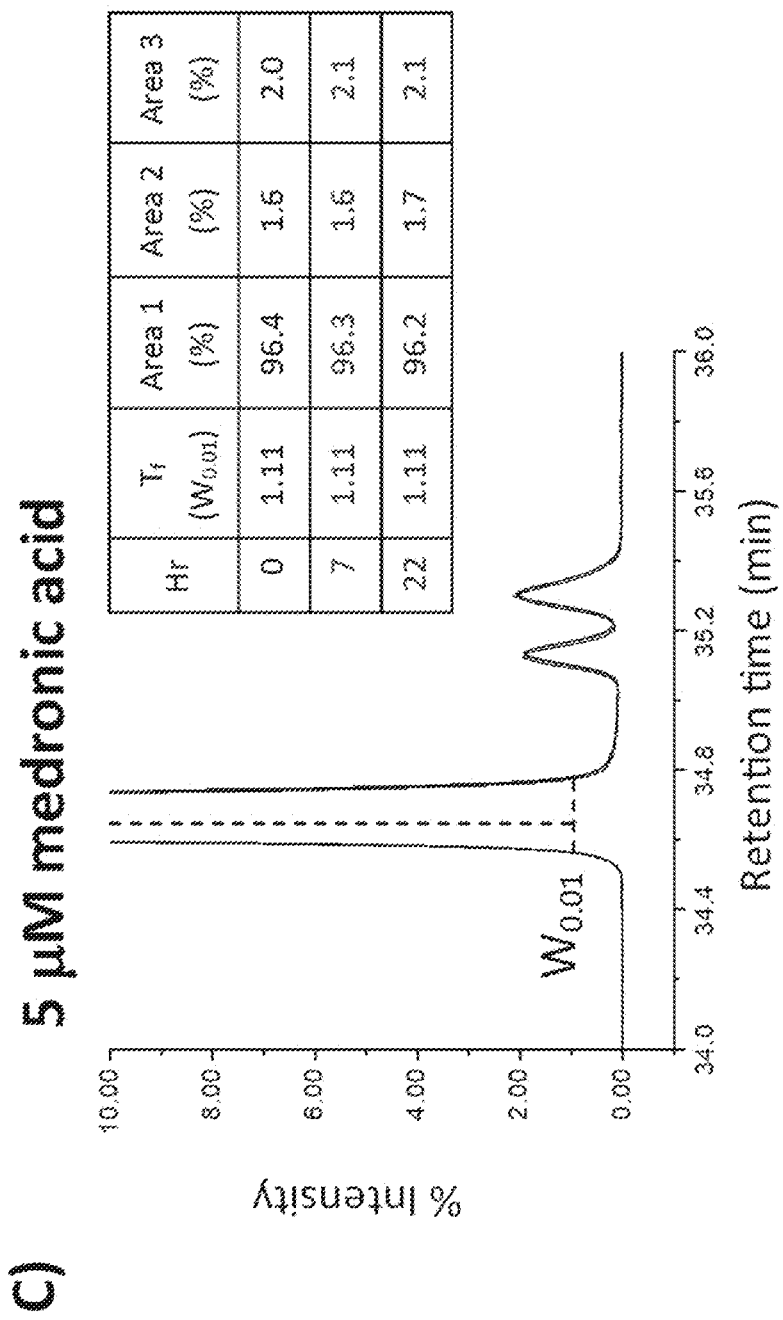
FIG. 8C is a chromatogram showing PENNYK (SEQ ID NO:4) peptide SIR overlays of 3 injections over time with 5 µM (0.9 ppm) medronic acid added into to the mobile phase, according to an illustrative embodiment of the technology. Tailing factor and relative peak area calculations are reported in the table insets. SIR overlays were time-aligned to facilitate comparison.

Citric acid and medronic acid were chosen as metal complexing agents to evaluate their impact on PENNYK (SEQ ID NO:4) tailing and area response. Using an abbreviated injection series, the same cleaning method and separation was employed as before. Mobile phases were prepared in the same fashion with the addition of the corresponding chelator at a concentration of 1 ppm. As Shown in FIGS. 8A-8C, both chelators had a significant impact in stabilizing the chromatographic performance of the PENNYK (SEQ ID NO:4) peptide in comparison to the previous experiment without the chelators (FIG. 8A). The observed performance gain was maintained from the initial injection greatly reducing experimental variability and corroborating the notion of metal-ion mediated adsorption. Without being bound by theory, the chelator complexes with metal ion impurities present in the mobile phase and acts as a solubilizing agent to prevent metal ion adsorption on fluidic surfaces or as a protecting group to mitigate metal-ion mediated adsorption. As shown in FIGS. 8B and 8C, citric acid and medronic acid were able to reduce peak tailing by as much as 40% over 22 hours at peak widths as low as 1% of peak height. The mitigation of tailing improved peak area consistency (% R.S.D.<3%) for the low abundant impurities with medronic acid exhibiting peak areas closer in agreement to the initial separation (FIG. 8A, 0 hr). It should be noted though that medronic acid was observed to negatively impact overall chromatographic performance and exhibit increased ionization efficiency differences and/or ion suppression artifacts.

Figure 9C:
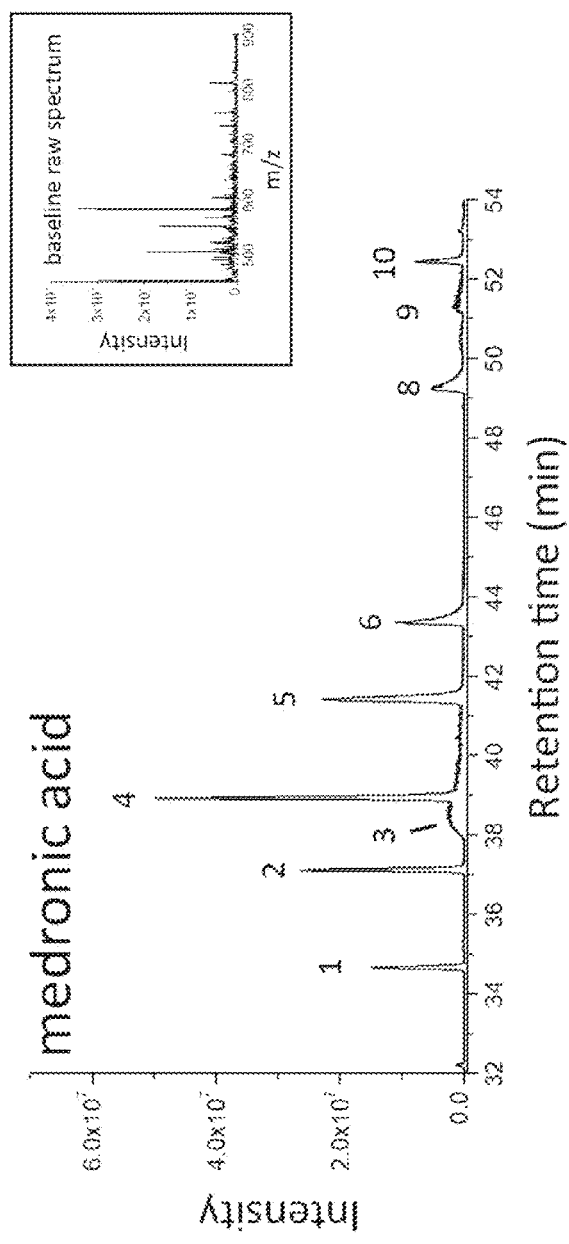
FIG. 9C is an extracted ion chromatogram (XIC) of major peptide species eluting within the region of the PENNYK (SEQ ID NO:4) peptide (T37) shown with 5 µM (0.9 ppm) medronic acid added into the mobile phase, according to an illustrative embodiment of the technology. Corresponding baseline spectrums at initial conditions were used to assess spectral contaminants and are shown in the inset figures.
Figure 9D:
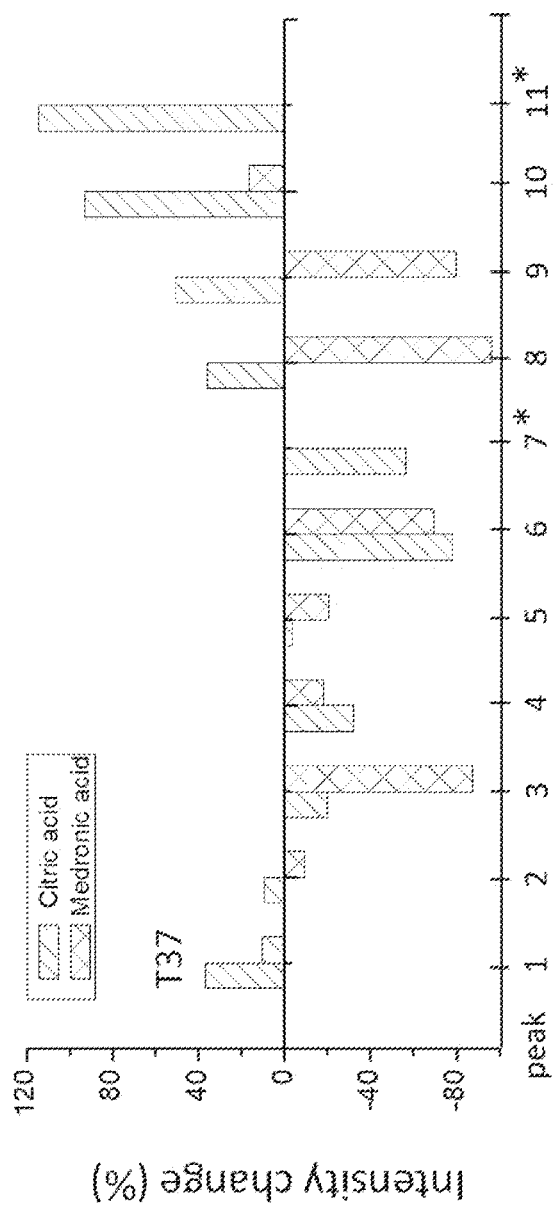
FIG. 9D is a graph showing the MS-response for citric acid and medronic acid normalized against the chromatogram containing no chelator and plotted as % intensity change, according to an illustrative embodiment of the technology. Asterisks indicate no peak detected in the XIC for medronic acid.

Extracted ion chromatograms (XICs) of major peptide species eluting in the nearby region (from 32 min to 54 min) of the PENNYK (SEQ ID NO:4) peptide were used to evaluate MS response of these peptides as shown in FIGS. 9A-9D. Inspection of the MS response of the PENNYK (SEQ ID NO:4) peptide (T37) showed both citric acid (FIG. 9B) and medronic acid (FIG. 9C) had an increased MS-response in comparison to the same run without a chelator present (FIG. 9A). In this instance, citric acid MS-response was 35% higher than the initial run while medronic acid only showed a 10% MS-response increase compared to the initial run. The lower MS-response exhibited by medronic acid relative to citric acid may be in part due to extraneous contaminants in the mobile phase. As shown in the inset images of FIGS. 9A-9C, combined MS spectra at initial conditions indicate a higher degree of spectral contamination is present in the mobile phases with chelators, particularly with the medronic acid. Without prior knowledge of the impurity profile of the commercial chelators, it can only be speculated that these extraneous components are contributing to ionization efficiency differences across experiments as shown in FIG. 9D. Contradictory to Hsiao et al. findings, this example showed medronic acid to have the unintended effect of increasing peak tailing in later eluting peptides, most notably in peak 3 as shown in FIG. 9C. An investigation of peak 3 identified it to be the alkylated hinge region peptide T20(HC):THTCPPCPAPELLGGPSVFLFPPKPK (SEQ ID NO 2). In contrast to this, citric acid peak profiles were generally preserved or improved across the same peptide species, most notably in the later eluting species (peaks 7-11). Interestingly, peak 3 did not show a marked increase in tailing in the absence of a chelator, despite containing a glutamic acid residue yet peptide T14(LC): VDNALQSGNSQESVTEQDSK (SEQ ID NO 3), which contains multiple glutamic acid and aspartic acid residues, exhibited similar tailing behavior as the PENNYK (SEQ ID NO:4) peptide (data not shown). Without being bound by theory, possible reasons for the observed differences may be due to varying acidic characteristics of the peptides, the carboxylic acid groups of the citric acid acting as a better mimic to peptides in comparison to the bisphosphonate structure of medronic acid, or chelator affinity/coordination characteristics. Given this, further investigation is needed to fully understand the role that chelator and peptide physicochemical properties play in the adsorption/coordination characteristics of peptides. However, the chromatographic performance gains provided by chelators in peptide mapping assays is evident, particularly for targeted assays of CQA's or routine monitoring scenarios where critical species are not impacted by secondary interactions in the presence of a chelator.

With supporting evidence of metal-ion mediated adsorption established, derivatives of citric acid including sodium citrate, ammonium citrate dibasic, ammonium citrate tribasic were assessed for impact on US/MS response and if chromatographic performance could be further improved. Interestingly, all derivatives explored showed increased fronting in comparison to citric acid and medronic acid. Given mobile phases were prepared at the same concentration of chelator and the same sample was used across the chelator set, the observed fronting appears to be related to the chelator rather than the sample or sample matrix. It should be noted though that the chelators were not of comparable purity, which may contributed to some of the observed differences. With respect to chromatographic performance the alternative chelators exhibited increased resolution between the native peak and impurities of the PENNYK (SEQ ID NO:4) peptide but were unable to improve resolution between the impurity peaks and in some instance's resolution decreased. As expected Na containing derivatives generated more salt adducts in MS-spectra in comparison to ammonium-based derivatives, yet neither type offered an advantage over citric acid or medronic acid in terms of chromatographic performance. Additive concentrations of up to 50 ppm were also evaluated without any additional benefits observed. It should be noted that 1 ppm appears to be the minimum amount of chelator required to have an observable effect on chromatography in the case of citric acid. Given these results, citric acid was selected given its optimal MS-response, comparable selectivity to native conditions, and absence of secondary interactions.

Figure 10:
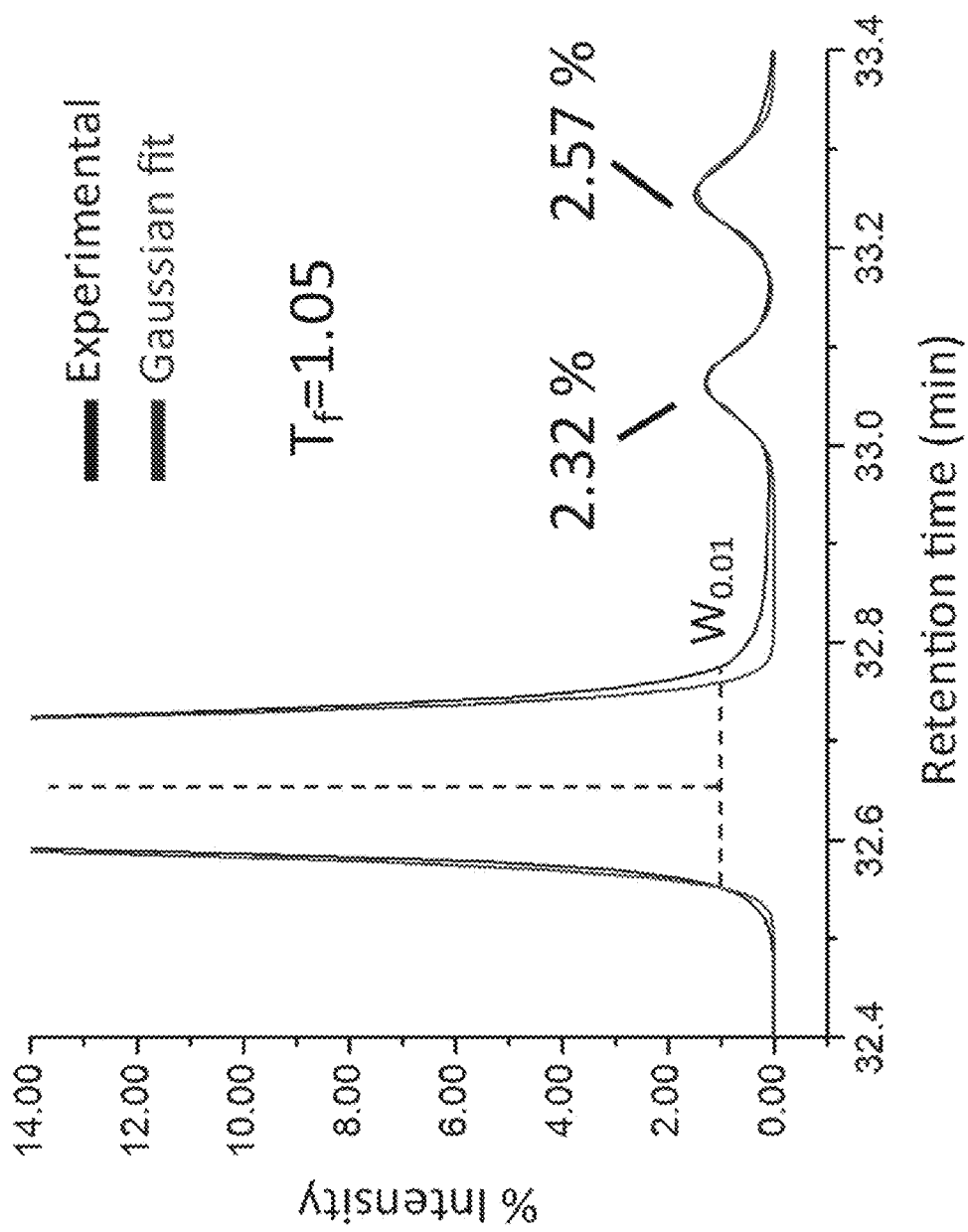
FIG. 10 is a chromatogram showing column loading impact on tailing under RPLC/MS conditions was evaluated using a reduced mass load, according to an illustrative embodiment of the technology. Tailing factor at $W_{0.01}$ was calculated to be 1.05 and was in good agreement with a Gaussian fit indicating minimal presence of tailing due to column loading effects.
Figure 11C:
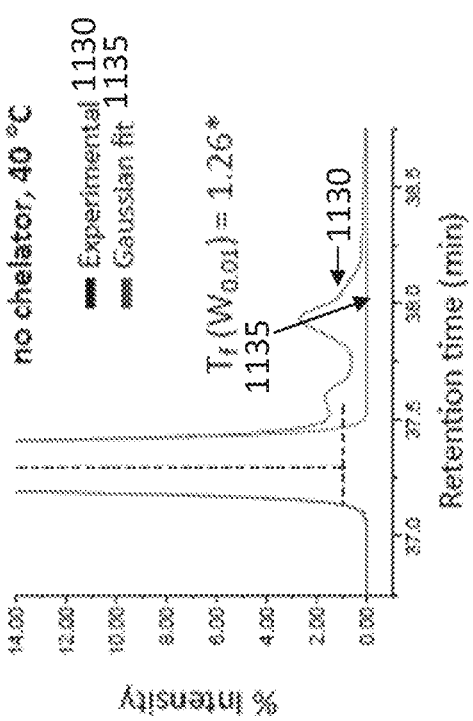
FIG. 11C is a chromatogram showing the experimental (1130) and Gaussian (1135) fits for no chelator at 40° C. for T37 (HC) GFYPSDIAVEWESNGQPENNYK (SEQ ID NO:1), according to an illustrative embodiment of the technology.
Figure 11A:
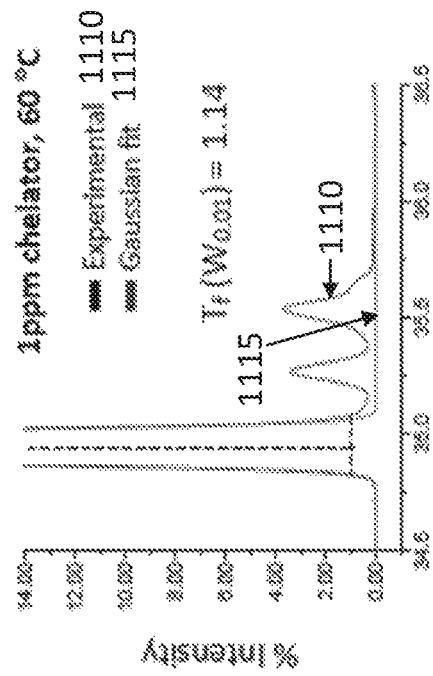
FIG. 11A is a chromatogram showing the experimental (1110) and Gaussian (1115) fits for 1 ppm chelator at 60° C. for T37 (HC) GFYPSDIAVEWESNGQPENNYK (SEQ ID NO:1), according to an illustrative embodiment of the technology. The impact of temperature on tailing was evaluated for peptide fragments T37 (FIGS. 11A-C) and T14 (FIGS. 11D-F) at 60° C. and 40° C. with and without chelator (citric acid) present in the mobile phase. Tailing factor was approximately preserved at lower temperatures in the presence of a chelator for both peptides with tailing only increasing up to 5%. T14 exhibited a 2.35-fold increase in tailing compared to T37 with a 1.10-fold increase in tailing in the absence of a chelator. Asterisks denote $T_f$ values that were extrapolated from plotted data.
Figure 11B:
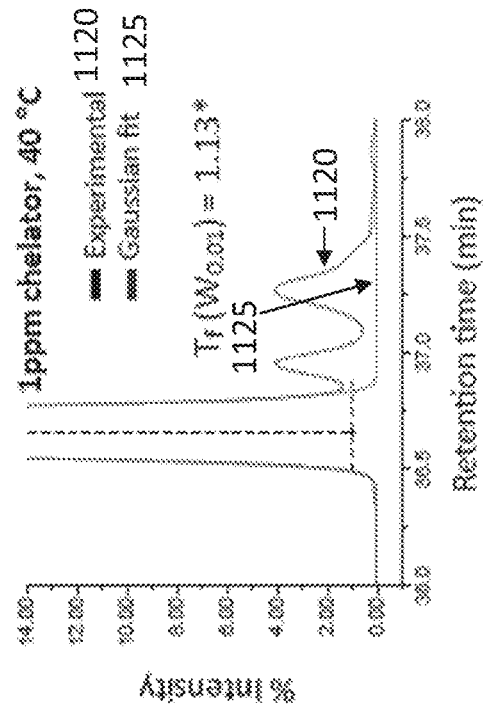
FIG. 11B is a chromatogram showing the experimental (1120) and Gaussian (1125) fits for 1 ppm chelator at 40° C. for T37 (HC) GFYPSDIAVEWESNGQPENNYK (SEQ ID NO:1), according to an illustrative embodiment of the technology.
Figure 12:
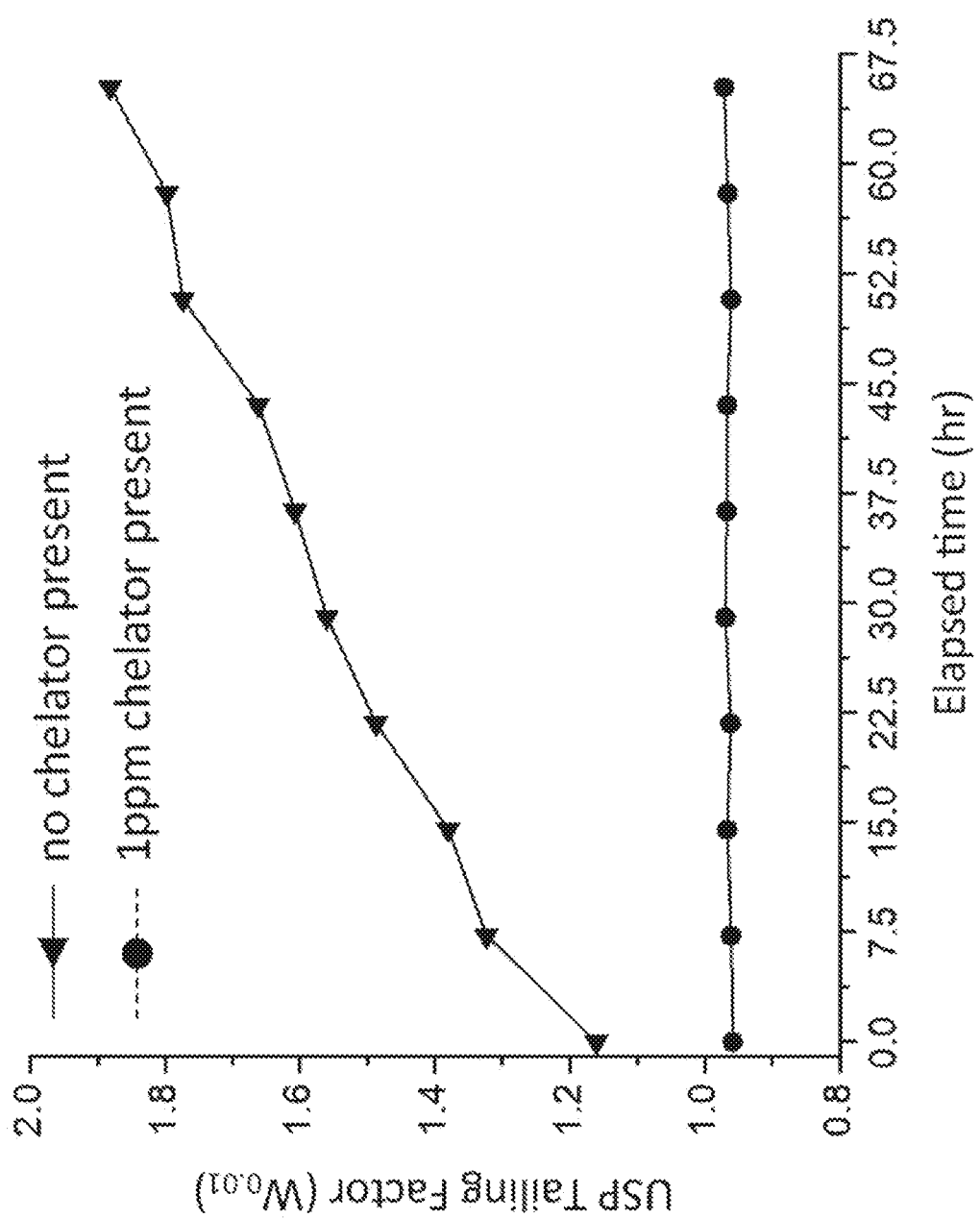
FIG. 12 is a graph showing tailing factor at $W_{0.01}$ was monitored for the PENNYK (SEQ ID NO:4) peptide over a 67-hr period with and without a chelator (citric acid) as a mobile phase additive using $H_2O$:NeCN, 0.1% FA v/v, according to an illustrative embodiment of the technology. Chromatographic performance was stabilized in the presence of a chelator with an average tailing factor of 0.96 (% RSD=0.43%).

To determine if the residual tailing observed in FIG. 8B was a result of column overload, a peptide map was performed at a reduced mass-load by diluting the sample with an equal amount of sample buffer. As shown in FIG. 10 peak tailing was only reduced by an additional 7% ($T_f=1.05$) with ideal Gaussian behavior in peak shape at peak widths as low as 1% of peak height. In addition to mass load, thermodynamic contribution to tailing was evaluated. As shown in FIGS. 11A-11C, peak tailing was conserved for the PENNYK (SEQ ID NO:4) peptide for separations performed in the presence of a chelator at a lower temperature of 40° C. with a $T_f$ value of 1.13. Although some peak broadening was observed, chromatographic profile and relative intensities were highly similar to the 60° C. data. In the absence of a chelator, T37 did exhibit a marginal increase in tailing of 11% at 40° C. ($T_f=1.26$) with relative intensities having closer resemblance to chromatographic profiles shown in FIGS. 6A and 6B. These observations suggest mass load and thermal contributions to residual peak tailing in the presence of chelator are minimal for the PENNYK (SEQ ID NO:4) peptide. Corroborating data was observed in peptide fragment T14 which exhibited similar behavior as shown in FIGS. 11D-11F. As a peptide containing acidic residues, the chromatographic profile of T14 was approximately conserved at lower temperatures with only a 6% increase in tailing in the presence of a chelator in contrast to over a 2-fold increase in tailing when the chelator was removed from the mobile phase. The lower sensitivity to tailing observed in T37 with and without a chelator present in comparison to T14 further supports the notion that metal-ion mediated adsorption is the main contributing factor to tailing of the PENNYK (SEQ ID NO:4) peptide in this study. To assess long-term stability of the assay under more strenuous conditions, a modified gradient was used to perform the peptide map over a 48 serial injection series. As shown in FIG. 12 peak tailing of a freshly prepared peptide digest was stable over 67 hr of continuous instrument use with an average tailing factor of 0.96 (% R.S.D.=0.43) at Wo01. It should be noted that peaks width at $W_{0.05}$ were experimentally determined to be Gaussian with a calculated tailing factor of 1.00 (% R.S.D.=0.64). The stabilizing effect of the chelator improved assay robustness with relative peak areas calculated at 2.32% (% R.S.D.=2.23) and 2.57% (% R.S.D.=3.97) for the leading and trailing impurity peaks. Collectively these results demonstrate using chelators as mobile phase additives offer a means to improve chromatographic performance for biomolecules sensitive to metal-ion mediated adsorption under formic acid-based RPLC conditions.

Conclusion

Metal-ion mediated adsorption has been an on-going area of research interest due to its impact on chromatographic performance and recovery of problematic compounds. In the biopharmaceutical industry peptide level separations of protein-based therapeutics are particularly challenging for closely eluting critical pairs as peak tailing and recovery directly impact assay robustness in terms of accuracy and sensitivity. Metal-ion mediated adsorption of critical peptides further complicates matters, notably in the manufacturing environment where limited resources are available for the development and validation of routine monitoring assays. In this context, assays that are robust and able to deliver accurate and consistent results are highly desirable. This example demonstrates metal complexing agents as mobile phase additives can significantly reduce metal-ion mediated adsorption of sensitive compounds for improved chromatographic performance in RPLC/MS-based separations. Specifically, peak tailing of the PENNYK (SEQ ID NO:4) peptide was reduced by as much as 40% at peak widths as low as 1% of peak height in the presence of citric acid at a concentration of 1 ppm in the mobile phase. Reduction of metal-ion mediated adsorption allowed for accurate quantitation of low-abundant deamidated impurities associated with the PENNYK (SEQ ID NO:4) peptide, a known critical quality attribute linked to drug product efficacy, with % R.S.D.s≤2.4%. Stabilizing properties of the chelator on chromatographic performance was demonstrated with an average peak tailing value of the native peak calculated at 1.0 (R.S.D. 0.64%) over a 48-injection series spanning 67 hours compared to deteriorating performance in the absence of a chelator with peak tailing increasing to 1.85 over the same time period. Furthermore, MS-response of the PENNYK (SEQ ID NO:4) peptide was improved with a 35% increase in MS signal intensity when using citric acid as a mobile phase additive increasing assay sensitivity in the detection of low-abundant critical impurities. Collectively, these results demonstrate separation conditions using chelators as mobile phase additives for improving chromatographic performance of peptides sensitive to metal-ion mediated adsorption in RPLC/MS-based separations. These conditions are particularly well suited for the manufacturing environment where assays inherently need to be robust and consistent to ensure drug products are safe and efficacious.

Example 2—Lauric Acid

Figure 14:
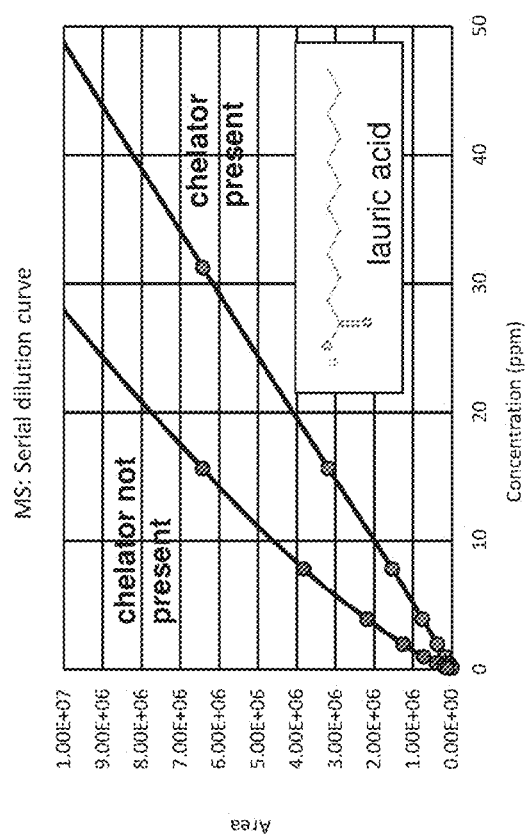
FIG. 14 shows a graph of the chelator addition to the mobile phase improving recovery of lauric acid (main fatty acid component of polysorbate 20 (PS-20)) to obtain a linear MS response, according to an illustrative embodiment of the technology.

The impact of mobile phase chelators was tested on different analyte types, for example, lauric acid. The same method was used as that outlined with respect to FIG. 2. Serial dilution of lauric acid starting at 4,000 ppm. 10 μL injection running isocratically at 75:25 acetonitrile:water with 1 ppm citric acid in mobile phase. FIG. 14 shows a graph of the chelator additional to the mobile phase improving recovery of lauric acid (main fatty acid component of polysorbate 20 (PS-20)) to obtain a linear MS response. This is useful for quantitation of impurities present in drug substance of drug product after finishing stages (cleaning or refinement). Without a linear response in the calibration curve, accurately quantitating the fatty acid using a multiple-point calibration curve or a single-point calibration curve is not possible.

Example 3—Comparison of Mobile Phase Additives

In this example, several different mobile phase additives were compared against 1 ppm citric acid. The system conditions are shown in FIG. 15.

Figure 16C:
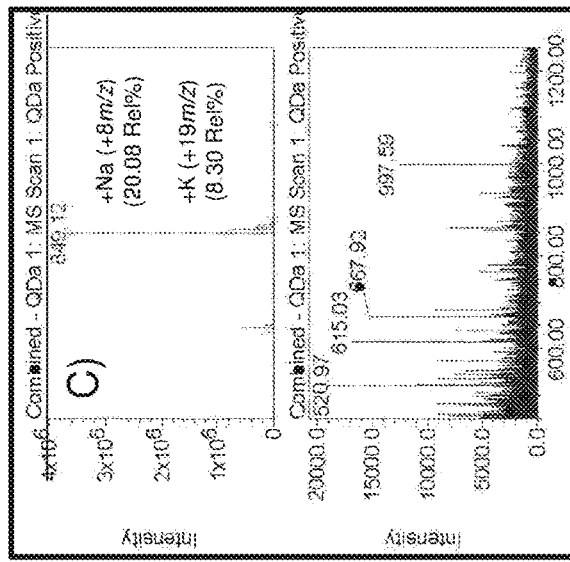
FIG. 16C is a combined QDa MS scan of the PENNYK (SEQ ID NO:4) peptide with 1 ppm citric acid mobile phase additive (top spectrum) and a combined spectrum of the baseline chromatogram noted in FIGS. 16A and 16B (bottom spectrum of FIG. 16C), according to an illustrative embodiment of the technology.
Figure 16D:
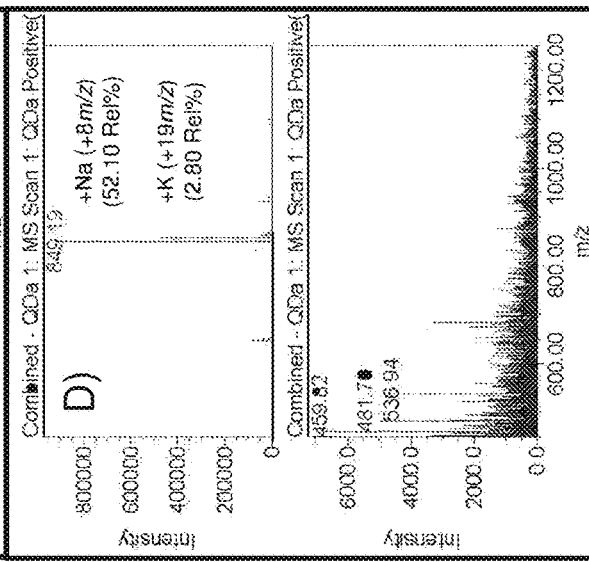
FIG. 16D is a combined QDa MS scan of the PENNYK (SEQ ID NO:4) peptide with 1 ppm sodium citrate mobile phase additive (top spectrum) and a combined spectrum of the baseline chromatogram noted in FIGS. 16A and 16B (bottom spectrum of FIG. 16D), according to an illustrative embodiment of the technology.

FIGS. 16A-16D show a comparison of 1 ppm citric acid to 1 ppm sodium citrate. As can be seen from a comparison of FIG. 16A to FIG. 16, the deamidated species of the PENNYK (SEQ ID NO:4) peptide showed worse resolution and some fronting is seen when 1 ppm of sodium citrate was used. In addition, a comparison of the top spectrum of FIG. 16C and the top spectrum of FIG. 16D shows that several adducts of the main peak that appear in FIG. 16C (1 ppm citric acid) are not present or present at significantly lower levels (e.g., Na and K) in FIG. 16D (1 ppm sodium citrate). The bottom spectra of FIGS. 16C and 16D look at the baseline region of the chromatogram to evaluate baseline noise intensity.

Figure 17C:
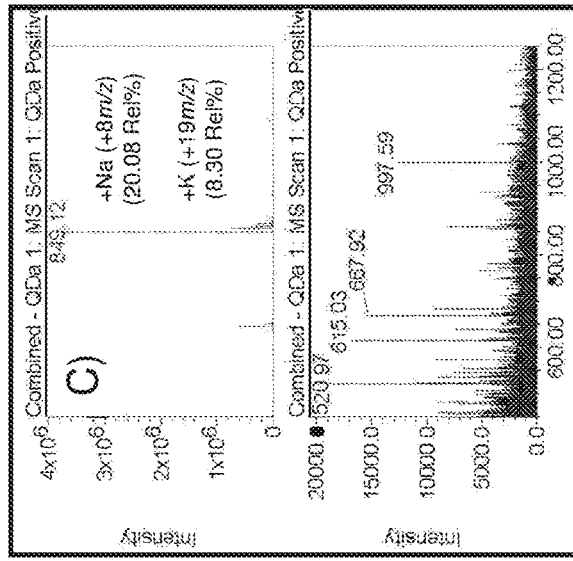
FIG. 17C is a combined QDa MS scan of the PENNYK (SEQ ID NO:4) peptide with 1 ppm citric acid mobile phase additive (top spectrum) and a combined spectrum of the baseline chromatogram (bottom spectrum), according to an illustrative embodiment of the technology. Although the baseline spectrum is not noted in FIGS. 17A and 17B, the same time area was used for the baseline as was used with respect to FIGS. 16A and 16B.
Figure 17D:
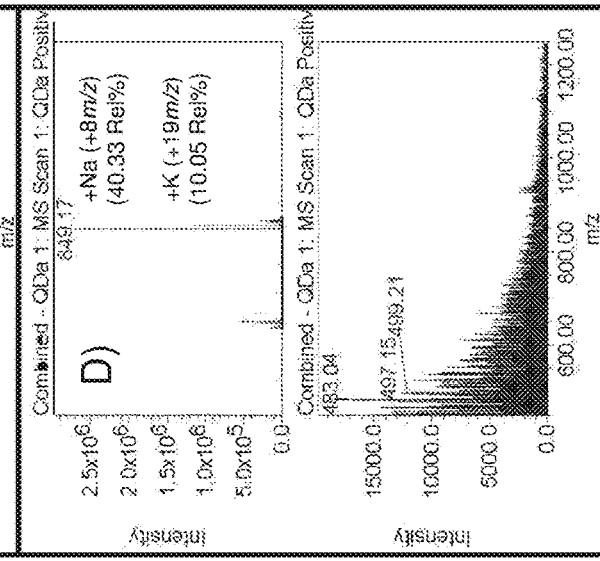
FIG. 17D is a combined QDa MS scan of the PENNYK (SEQ ID NO:4) peptide with 1 ppm isocitrate mobile phase additive (top spectrum) and a combined spectrum of the baseline chromatogram (bottom spectrum), according to an illustrative embodiment of the technology. Although the baseline spectrum is not noted in FIGS. 17A and 17B, the same time area was used for the baseline as was used with respect to FIGS. 16A and 16B.

FIGS. 17A-17D show a comparison of 1 ppm citric acid to 1 ppm isocitrate. As can be seen from a comparison of FIG. 17A to FIG. 17B, the deamidated species of the PENNYK (SEQ ID NO:4) peptide showed worse resolution and some fronting is seen when 1 ppm of isocitrate was used. In addition, a comparison of the top spectrum of FIG. 17C and the top spectrum of FIG. 17D shows that several adducts of the main peak that appear in FIG. 17C (1 ppm citric acid) are not present or present at significantly lower levels (e.g., Na and K) in FIG. 17D (1 ppm isocitrate). The bottom spectra of FIGS. 17C and 17D look at the baseline region of the chromatogram to evaluate baseline noise intensity.

FIGS. 18A-18D show a comparison of 1 ppm citric acid to 1 ppm ammonium citrate dibasic. As can be seen from a comparison of FIG. 18A to FIG. 18B, the deamidated species of the PENNYK (SEQ ID NO:4) peptide showed worse resolution and some fronting is seen when 1 ppm of ammonium citrate dibasic was used. In addition, a comparison of the top spectrum of FIG. 18C and the top spectrum of FIG. 18D shows that several adducts of the main peak that appear in FIG. 18C (1 ppm citric acid) are not present or present at significantly lower levels (e.g., Na and K) in FIG. 18D (1 ppm ammonium citrate dibasic). The bottom spectra of FIGS. 18C and 18D look at the baseline region of the chromatogram to evaluate baseline noise intensity.

Figures 19C, 19D:
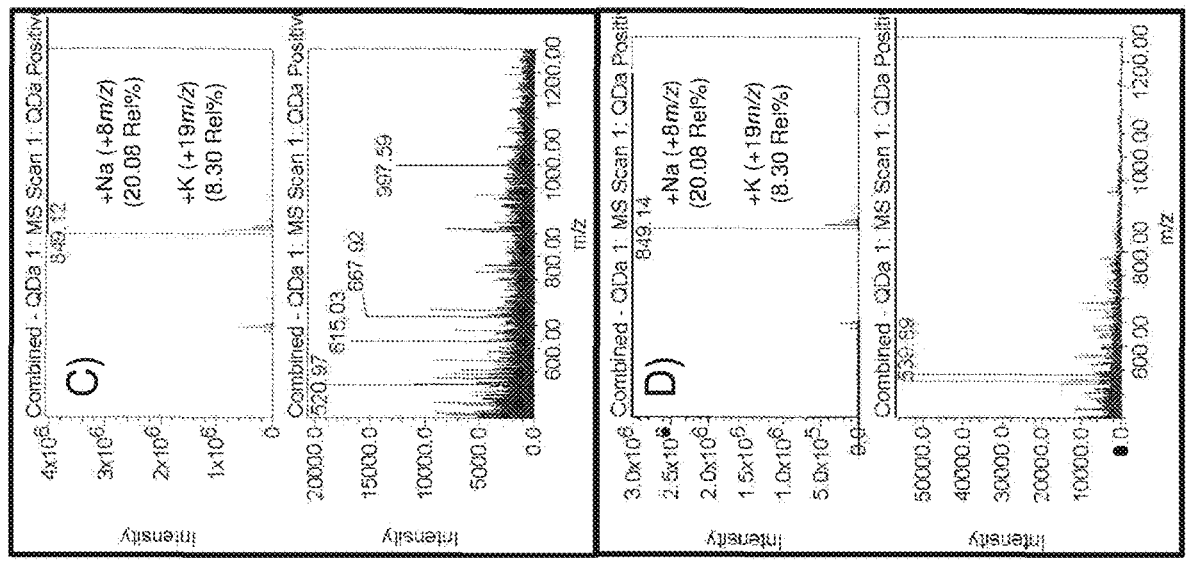
FIG. 19C is a combined QDa MS scan of the PENNYK (SEQ ID NO:4) peptide with 1 ppm citric acid mobile phase additive (top spectrum) and a combined spectrum of the baseline chromatogram (bottom spectrum), according to an illustrative embodiment of the technology. Although the baseline spectrum is not noted in FIGS. 19A and 19B, the same time area was used for the baseline as was used with respect to FIGS. 16A and 16B.
FIG. 19D is a combined QDa MS scan of the PENNYK (SEQ ID NO:4) peptide with 1 ppm ammonium citrate tribasic mobile phase additive (top spectrum) and a combined spectrum of the baseline chromatogram (bottom spectrum), according to an illustrative embodiment of the technology. Although the baseline spectrum is not noted in FIGS. 19A and 19B, the same time area was used for the baseline as was used with respect to FIGS. 16A and 16B.

FIGS. 19A-19D show a comparison of 1 ppm citric acid to 1 ppm ammonium citrate tribasic. As can be seen from a comparison of FIG. 19A to FIG. 19B, the deamidated species of the PENNYK (SEQ ID NO:4) peptide showed worse resolution and some fronting is seen when 1 ppm of ammonium citrate tribasic was used. In addition, a comparison of the top spectrum of FIG. 19C and the top spectrum of FIG. 19D shows that several adducts of the main peak that appear in FIG. 19C (1 ppm citric acid) are not present or present at significantly lower levels (e.g., Na and K) in FIG. 19D (1 ppm ammonium citrate tribasic). The bottom spectra of FIGS. 19C and 19D look at the baseline region of the chromatogram to evaluate baseline noise intensity.

Figure 20A:
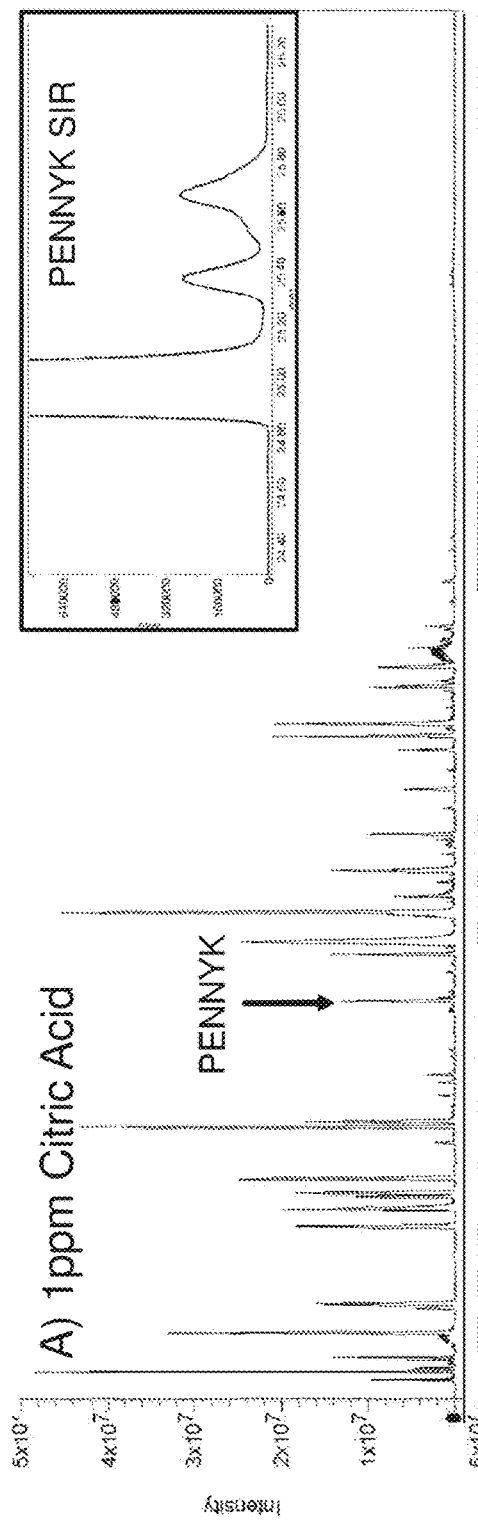
FIG. 20A is a chromatogram of the PENNYK (SEQ ID NO:4) peptide and is deamidated species (inset) with 1 ppm citric acid mobile phase additive, according to an illustrative embodiment of the technology.
Figure 20B:
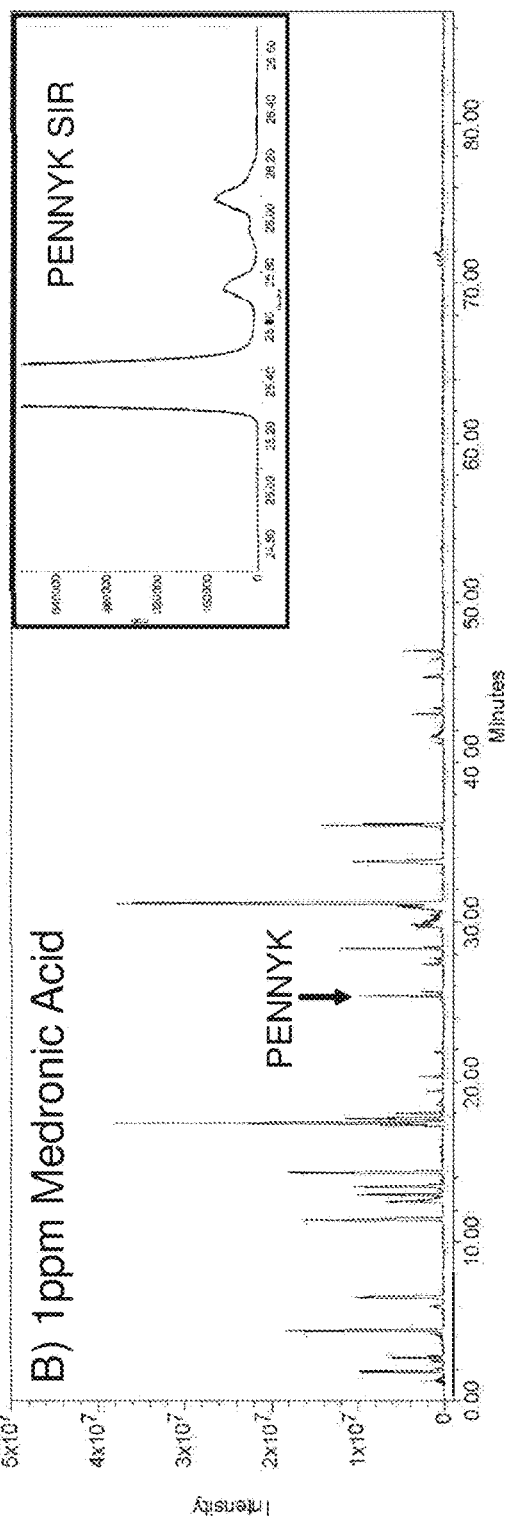
FIG. 20B is a chromatogram of the PENNYK (SEQ ID NO:4) peptide and is deamidated species (inset) with 1 ppm medronic acid mobile phase additive, according to an illustrative embodiment of the technology.

FIGS. 20A-20D show a comparison of 1 ppm citric acid to 1 ppm medronic acid. As can be seen from a comparison of FIG. 20A to FIG. 20B, the deamidated species of the PENNYK (SEQ ID NO:4) peptide showed comparable resolution of shoulder peaks when 1 ppm of medronic acid was used. In addition, a comparison of the top spectrum of FIG. 20C and the top spectrum of FIG. 20D shows that several adducts of the main peak that appear in FIG. 20C (1 ppm citric acid) are not present in FIG. 20D (1 ppm medronic acid). The bottom spectra of FIGS. 20C and 20D look at the baseline region of the chromatogram to evaluate baseline noise intensity.

Figure 21C:
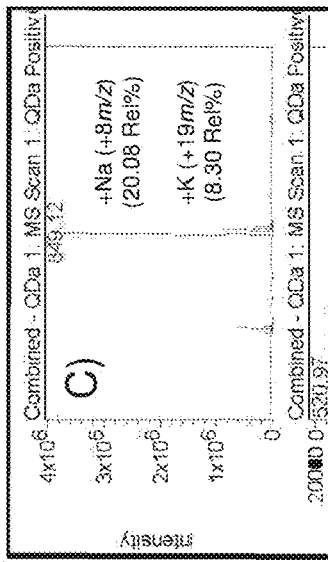
FIG. 21C is a combined QDa MS scan of the PENNYK (SEQ ID NO:4) peptide with 1 ppm citric acid mobile phase additive (top spectrum) and a combined spectrum of the baseline chromatogram (bottom spectrum), according to an illustrative embodiment of the technology. Although the baseline spectrum is not noted in FIGS. 21A and 21B, the same time area was used for the baseline as was used with respect to FIGS. 16A and 16B.
Figure 21D:
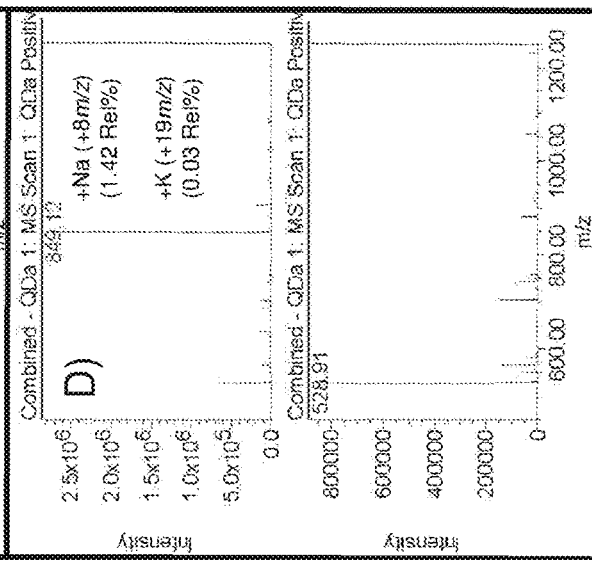
FIG. 21D is a combined QDa MS scan of the PENNYK (SEQ ID NO:4) peptide with 5 µM Agilent InfinityLab mobile phase additive (top spectrum) and a combined spectrum of the baseline chromatogram (bottom spectrum), according to an illustrative embodiment of the technology. Although the baseline spectrum is not noted in FIGS. 21A and 21B, the same time area was used for the baseline as was used with respect to FIGS. 16A and 16B.

FIGS. 21A-21D show a comparison of 1 ppm citric acid to 5 μM Agilent InfinityLab Additive. As can be seen from a comparison of FIG. 21A to FIG. 21B, the deamidated species of the PENNYK (SEQ ID NO:4) peptide showed comparable resolution but with lower intensity for the impurities but better resolution for the main peak is seen when 5 μM Agilent InfinityLab Additive was used. This could be an artifact of suppression as only the top portion of the peak is seen and hence it is a narrower peak. In addition, a comparison of the top spectrum of FIG. 21C and the top spectrum of FIG. 21D shows that several adducts of the main peak that appear in FIG. 21C (1 ppm citric acid) are not present in FIG. 21D (5 μM Agilent InfinityLab Additive) (the baseline increased due to strong spectral contamination—see Example 2). The bottom spectra of FIGS. 21C and 21D look at the baseline region of the chromatogram to evaluate baseline noise intensity.

Those skilled in the art will recognize, or be able to ascertain using no more than routine experimentation, numerous equivalents to the specific procedures described herein. Such equivalents were considered to be within the scope of this technology and are covered by the following claims. The contents or all references, issued patents, and published patent applications cited throughout this application are hereby incorporated by reference.

What is claimed is:

1. A method of analyzing a sample comprising an intact protein for peptide mapping, the method comprising:
    reducing the intact protein in the sample to a linear chain of amino acids;
    enzymatically treating the linear chain of amino acids to produce a mixture of peptides;
    injecting the sample comprising the mixture of peptides into a mobile phase comprising from about 1 ppm to about 10 ppm of citric acid;
    separating the mixture of peptides using reverse-phase liquid chromatography; and
    analyzing the separated peptides using a mass spectrometer, an ultra-violet detector, a fluorescence detector, or a combination thereof.

2. The method of claim 1, wherein at least one peptide in the mixture of peptides comprises a charged amino acid residue.

3. The method of claim 2, wherein the charged amino acid residue is aspartic acid, glutamic acid, or iso-aspartic acid.

4. The method of claim 1, wherein at least one peptide in the mixture of peptides has a net charge.

5. The method of claim 4, wherein the net charge is negative.

6. The method of claim 1, wherein the protein is a monoclonal antibody.

7. The method of claim 1, wherein the protein is a synthetic protein or a recombinant protein.

8. The method of claim 1, wherein the mixture of peptides comprises SEQ ID NO:4 and deamidated forms of SEQ ID NO:4.

9. The method of claim 1, wherein the linear chain of amino acids is enzymatically treated with trypsin, Lys-C, Asp-N, or a combination thereof.

10. The method of claim 1, wherein chromatographic performance is maintained over a period of about 2 days to about 3 days with an average United States Pharmacopeia (USP) tailing value of about 0.95 to about 1.30.

11. The method of claim 1, wherein chromatographic performance is maintained over about 48 consecutive injections with an average United States Pharmacopeia (USP) tailing value of about 0.95 to about 1.30.

12. The method of claim 1, wherein the mixture of peptides comprises a peptide and a deamidated species of the peptide.

13. The method of claim 1, wherein a concentration of citric acid in the mobile phase is about 1 ppm.

14. The method of claim 1, wherein the mobile phase further comprises formic acid, acetic acid, water, acetonitrile, methanol, isopropanol, n-propanol, trifluoroacetic acid, difluoroacetic acid, or a combination thereof.

15. The method of claim 1, further comprising passivating a reverse-phase chromatography column with citric acid prior to separating the mixture of peptides.

\* \* \* \* \*